(12) United States Patent
McKew et al.

(10) Patent No.: US 6,984,735 B2
(45) Date of Patent: Jan. 10, 2006

(54) PROCESS FOR MAKING AN ALDEHYDE

(75) Inventors: John C. McKew, Arlington, MA (US); Steven Y. Tam, Wellesley, MA (US); Katherine L. Lee, West Newton, MA (US); Lihren Chen, Cambridge, MA (US); Paresh Thakker, Boston, MA (US); Fuk-Wah Sum, Pomona, NY (US); Mark Behnke, Sommerville, MA (US); Baihua Hu, Audubon, PA (US); James D. Clark, Acton, MA (US); Wei Li, Acton, MA (US)

(73) Assignee: Wyeth, Madison, NJ (US)

( * ) Notice: Subject to any disclaimer, the term of this patent is extended or adjusted under 35 U.S.C. 154(b) by 17 days.

(21) Appl. No.: 10/722,782

(22) Filed: Nov. 26, 2003

(65) Prior Publication Data

US 2004/0082785 A1 Apr. 29, 2004

Related U.S. Application Data

(63) Continuation-in-part of application No. 10/302,636, filed on Nov. 22, 2002, now Pat. No. 6,797,708.

(60) Provisional application No. 60/334,588, filed on Dec. 3, 2001.

(51) Int. Cl.
 C07D 215/38 (2006.01)
 C07D 217/12 (2006.01)
(52) U.S. Cl. .................. 544/334; 546/146; 546/169; 546/315; 548/194; 548/236; 548/248; 568/316
(58) Field of Classification Search ................ 544/334; 546/169, 146, 315; 548/194, 236, 248; 568/316
See application file for complete search history.

(56) References Cited

U.S. PATENT DOCUMENTS

| | | |
|---|---|---|
| 3,505,354 A | 4/1970 | Doebel et al. |
| 3,629,284 A | 12/1971 | Yamamoto et al. |
| 4,271,263 A | 6/1981 | Goettert |
| 4,654,360 A | 3/1987 | Greenhouse et al. |
| 4,894,386 A | 1/1990 | Brown et al. |
| 5,081,145 A | 1/1992 | Guindon et al. |
| 5,166,170 A | 11/1992 | Tegeler et al. |
| 5,212,195 A | 5/1993 | Clark et al. |
| 5,229,516 A | 7/1993 | Musser et al. |
| 5,288,743 A | 2/1994 | Brooks et al. |
| 5,290,798 A | 3/1994 | Guillard et al. |
| 5,322,776 A | 6/1994 | Knopf et al. |
| 5,332,755 A | 7/1994 | Butler et al. |
| 5,354,677 A | 10/1994 | Knopf et al. |
| 5,380,739 A | 1/1995 | Clark et al. |
| 5,420,289 A | 5/1995 | Musser et al. |
| 5,424,329 A | 6/1995 | Boschelli et al. |
| 5,482,960 A | 1/1996 | Berryman et al. |
| 5,641,800 A | 6/1997 | Bach et al. |

FOREIGN PATENT DOCUMENTS

| | | |
|---|---|---|
| CH | 484111 | 1/1970 |
| DE | 18 16 335 A | 7/1970 |
| DE | 43 38 770 A1 | 5/1995 |
| EP | 0 337 766 A1 | 10/1989 |
| EP | 0 337 767 A1 | 10/1989 |
| EP | 0 620 215 A1 | 10/1994 |
| FR | 1 492 929 | 7/1967 |
| WO | WO 91/06537 A2 | 5/1991 |
| WO | WO 93/23391 A1 | 11/1993 |
| WO | WO 95/13266 A1 | 5/1995 |
| WO | WO 98/05637 A1 | 2/1998 |
| WO | WO 98/08818 A1 | 3/1998 |
| WO | WO 99/43651 A2 | 9/1999 |
| WO | WO 99/43654 A2 | 9/1999 |
| WO | WO 99/43672 A1 | 9/1999 |

OTHER PUBLICATIONS

Saldabols et al., Study of the Reaction of Dimethyl Sulfoxide with Bromo- and Dibromomethyl aryl ketones, Sery Sernistykh Neftei, 13th 1994, 188.*
Roy et al., Further Studies on Anti-Inflammatory Activity of Two Potent Indan-1-Acetic Acids, Ind. J. Physiol. Pharmac., Jul.-Sep. 1982, vol. 28, No. 3, pp 207-214.
Draheim et al., Indole Inhibitors of Human Nonpancreatic Secretory Phospholipase $A_2$. 3 Indole-3-glyoxamides, J. Med. Chem 1996, vol. 39, No. 26, pp 5159-5175.
Dillard et al., Indole Inhibitors of Human Nonpancreatic Secretory Phospholipase $A_2$. 2. Indole-3-acetamides with Additional Functionality, J. Med.chem. 1996, vol. 39, No. 26, pp 5137-5158.
Dillard et al, Indole Inhibitors of Human Nonpancreatic Secretory Phospholipase $A_2$. 1. Indole-3-acetamides, J. Med. Chem., 1996, vol. 39, No. 26, pp 5119-5136.
Schevitz et al., Nature Structural Biology, vol. 2, No. 2, Jun. 1995, pp 458-465.
Doebel et al., J. Med. Chem., 1972, vol. 15, No. 10, pp 1081-1082.

(Continued)

*Primary Examiner*—Hohann Richter
*Assistant Examiner*—Chukwuma Nwaonicha
(74) *Attorney, Agent, or Firm*—Cozen O'Connor

(57) ABSTRACT

A process for making an aromatic aldehyde in which a sulfoxide is reacted with a dihalogenated aromatic compound in the absence of an effective amount of an activating reagent. The aldehyde may then be used to make other compounds, such as a compound that acts as a cPLA inhibitor.

14 Claims, No Drawings

OTHER PUBLICATIONS

Xi et al., Functionalized Deep-Cavity Cavitands, J. Org. Chem. 1999, 64, pp 9286-9288.

Steinhoff et al., Mechanistic Study of Alcohol Oxidation by the $Pd(OAc)_2/O_2/DMSO$ Catalyst System and Implications for the Development of Improved Aerobic Oxidation Catalysts, J. Am. Chem.. Soc., vol. 124, No. 5, 2002, pp 766-767.

Arterburn et al., Selective Rhenium-Catalyzed Oxidation of Secondary Alcohols with Methyl Sulfoxide in the Presence of Ethylene Glycol, a Convenient One-Pot Synthesis of Ketals, Organic Letters, 1999, vol. 1, No. 5, pp 769-771.

Peterson et al., Palladium-Catalyzed Oxidation of Primary and Secondary Allylic and Benzylic Alcohols, J. Org. Chem. 1998, 63, pp 3185-3189.

Langer et al., Synthesis of High-specific-radioactivity 4- and 6-[$^{18}$F]fluorometaraminol- PET Tracers for the Adrenergic Nervous System of the Heart, Bioorganic & Medicinal Chemistry, 9, 2001, pp 677-694.

Adediran et al., The Synthesis and Evaluation of Benzofuranones as β-Lactamase Substrates, Bioorganic & Medicinal Chemistry, 9, 2001, pp 1175-1183.

Goodman et al., Self-Assembling, Chromogenic Receptors for the Recognition of Dicarboxylic Acid, J. Am. Chem. Soc., 1995, 117, pp 8447-8455.

Chung et al., Synthesis of 3-Fluoro-2-substituted amino-5, 12-dihydro-5-oxobenzoxazolo[3,2-α] quinoline-6-carboxylic Acids Employing the Tandem Double Ring Closure Reaction of N-Acetyl-N-(2-hydroxyphenyl) anthranilic Acid as the Key Step, Tetrahedron vol. 51, No. 46, pp 12549-12562, 1995, Elsevier Science Ltd, printed in Great Britain.

Pfitzner et al., Sulfoxide-Carbodiimide Reactions. I. A Facile Oxidation of Alcohols, J. Am. Chem Society, 87:24, Dec. 20, 1965, pp 5661-5670.

Epstein et al., Dimethyl Sulfoxide Oxidation, Chemical Reviews, vol. 67, No. 3, May 25, 1967, pp 247-260.

Pfitzner et al., Sulfoxide-Carbodiimide Reactions. II. Scope of the Oxidation Reaction[1], J. Am. Chem. Society, 87:24, Dec. 20, 1965, pp 5670-5678.

Fenselau et al., Sulfoxide-Carbodiimide Reactions. III.[1] Mechanism of the Oxidation Reaction, J. Am. Chem Society, 88:8, Apr. 20, 1966, pp 1762-1765.

Albright et al., Dimethyl Sulfoxide-Acid Anhydride Mixtures for the Oxidation of Alcohols, J. Am. Chem. Society, 89:10, May 10, 1967, pp 2416-2423.

Omura et al., Dimethyl Sulfoxide-Trifluoroacetic Anhydride: a New Reagent for Oxidation of Alcohols to Carbonyls[1], J. Org. Chem., vol. 41, No. 6, 1976, pp 957-962.

Padwa et al., Sulfoxonium Salts as Reagents for the Oxidation of Primary and Secondary Alcohols to Carbonyl Compounds, J. Org. Chem., vol. 39, No. 13, 1974, pp 1977-1979.

Boyer et al., Sulfur Trioxide in the Oxidation of Alcohols by Diemthyl Sulfoxide, J. Am. Chem. Society, 89:21, Oct. 11, 1967, pp 5505-5506.

\* cited by examiner

PROCESS FOR MAKING AN ALDEHYDE

The present application is a continuation-in-part of application U.S. Ser. No. 10/302,636 filed Nov. 22, 2002, now U.S. Pat. No. 6,797,708 the entire contents of which is herein incorporated by reference, which claims priority from the provisional application U.S. Ser. No. 60/334,588 filed Dec. 3, 2001, now abandoned.

The present invention relates to a process for reacting a dihalogenated compound with an organic sulfoxide compound to form an aldehyde compound.

BACKGROUND OF THE INVENTION

Aromatic aldehyde compounds are useful for making numerous other compounds, as well as for their own properties. For example, in Method A shown in the description below an aldehyde undergoes chemical reactions to form a compound which is a cPLA$_2$ inhibitor having a variety of therapeutic uses, as described below. It is often necessary or desirable to obtain such an aldehyde from a corresponding dihalogenated aromatic compound.

Certain methods for converting a dihalogenated aromatic compound to its corresponding aldehyde are known. Typically, they require harsh reaction conditions, which generally involve high temperatures and as a strong acid, such as concentrated sulfuric acid, or a strong base, such as aqueous sodium hydroxide. Examples of these methods are found in Chung and Kim, *Tetrahedron*, 1995, 51(46), 12549–12562, and Goodman, et al., *J. Am. Chem. Soc.*, 1995, 117, 8447–8455.

Conversion of dihalo aromatics to aldehydes has been shown to occur by reaction with sodium carbonate (Adediran, et al., *Bioorg. Med. Chem.*, 2001, 42, 1175–1183), and with sodium bicarbonate (Langer, et al., *Bioorg. Med. Chem.*, 2001, 9, 677–694), with heavy metal salts like silver nitrate (Semmelhack, et al., *J. Am. Chem. Soc.* 1994, 116, 7108).

It has been reported that benzal bromides may be hydrolyzed to the corresponding benzaldehyde using potassium carbonate in dimethylsulfoxide (DMSO) solvent (Huaping Xi, et al., *J. Org. Chem.*, 1999, 64(29), 9286–9288). In this reaction, the potassium carbonate hydrolyzed the dibromo compounds to the corresponding aldehydes.

Harsh reaction conditions are not suitable for all dihalogenated aromatics because undesirable side reactions may occur. Furthermore, it is safer and less expensive to avoid using strong acids and bases and high temperatures. Although mild reaction conditions have been reported, development of good procedures for such transformation is desirable.

Sulfoxides are often used as an oxygen-donating agent in organic synthesis, for example, to convert structurally diverse alcohols to their corresponding carbonyl compounds in the presence of activating reagents, such as transition metal catalysts (Steinhoff, et al., *J. Amer. Chem. Soc.*, 2002, 124(5), 766–767; Arterburn and Perry, *Org. Lett.*, 1999, 1(5), 769–771.), or dicyclohexylcarbodiimide (Pfitzner and Moffatt, *J. Amer. Chem. Soc.*, 1965, 87(24), 5661–5670). Activation is necessary for the sulfoxide to effect the desired transformation.

SUMMARY OF THE INVENTION

The present invention comprises reacting a dihalomethyl compound with a sulfoxide in the absence of an effective amount of an activating reagent to form the corresponding aldehyde, as shown in the reaction:

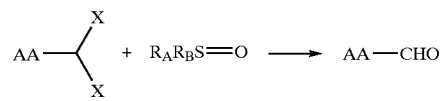

wherein

AA represents an aryl group, or non-aromatic functional groups such as alkenyl or alkynyl group;

X represents F, Cl, Br, or I; and $R_A$ and $R_B$ are each an alkyl or aryl group independently selected from the group consisting of $C_1$–$C_6$ alkyl optionally substituted by a $C_4$–$C_8$ cycloalkyl or phenyl group, $C_4$–$C_8$ cycloalkyl optionally substituted by up to two $C_1$–$C_3$ alkyl groups, and phenyl optionally substituted by up to five $C_1$–$C_3$ alkyl groups. $R_A$ and $R_B$ also may have one or more chiral centers.

Preferred aryl groups in the practice of this invention include phenyl, naphthyl, indolyl, biphenyl, pyridinyl, pyrrolyl, quinolinyl, isoquinolinyl, pyrimidinyl, furyl, oxazolyl, thioazolyl, isoxazolyl and the like, all of which may be substituted or unsubstituted. Preferred non-aromatic functional groups include straight, branched, cyclic and bicyclic alkenyl and alkynyl groups having from 2 to 12 carbon atoms.

An activating reagent is any chemical entity that interacts chemically with the sulfoxide to promote oxygen transfer from the sulfoxide to the dihalogenated aromatic compound. Activating agents may include transition metal catalysts, acids, bases, dehydration agents, and organic or inorganic entities that will form a complex or transition state with DMSO.

DETAILED DESCRIPTION OF THE INVENTION

Preferred sulfoxides in the practice of this invention include DMSO, tetramethylene sulfoxide, diphenyl sulfoxide, methyl phenyl sulfoxide, and the like.

In the reaction above, AA is most preferably substituted or unsubstituted phenyl, biphenyl or indolyl. Preferably, each of $R_A$ and $R_B$ is unsubstituted, and most preferably each is independently phenyl, methyl, ethyl or tetramethylene.

In one preferred embodiment of this invention, AA is phenyl optionally substituted with from one to three, preferably one, halogen, cyano, nitro, hydroxy, $R_C$ alkyl, —C(O)OR$_C$ alkyl, —NR$_C$R$_D$, —C(O)NR$_C$R$_D$ amide, S(O)$_2$R$_C$R$_D$, NR$_1$C(O)NR$_C$R$_D$, or —OC(O)NR$_C$R$_D$ group, where $R_C$ and $R_D$ are each $C_1$–$C_4$ alkyl and $R_1$ has the meaning set forth below; the sulfoxide reactant is DMSO; and the reaction proceeds at about 20–120° C. for about 10 min.–18 hours. The table below provides the reaction conditions and results of a number of examples of this embodiment:

| Entry | Reactant | Product | Temp./Time | Yield (%) |
|---|---|---|---|---|
| 1 | Dibromomethyl-benzene | Benzaldehyde | 100° C./2 hr | 95 |
| 2 | 1-Dibromomethyl-3-fluoro-benzene | 3-Fluoro-benzaldehyde | 120° C./12 hr | 92 |

-continued

| Entry | Reactant | Product | Temp./Time | Yield (%) |
|---|---|---|---|---|
| 3 | 1-Dibromomethyl-3-chloro-benzene | 3-Chloro-benzaldehyde | 100° C./2 hr | 95 |
| 4 | 1-Dibromomethyl-3-bromo-benzene | 3-Bromo-benzaldehyde | 120° C./1 hr | 95 |
| 5 | 1-Dibromomethyl-4-fluoro-benzene | 4-Fluoro-benzaldehyde | 120° C./12 hr | 93 |
| 6 | 1-Dibromomethyl-4-chloro-benzene | 4-Chloro-benzaldehyde | 100° C./10 hr | 96 |
| 7 | 1-Dibromomethyl-2-fluoro-benzene | 2-Fluoro-benzaldehyde | 120° C./18 hr | 100 |
| 8 | 1-Dibromomethyl-4-ethyl-benzene | 4-Ethyl-benzaldehyde | 100° C./5 hr | 80 |
| 9 | 4-Dibromomethyl-benzoic acid ethyl ester | 4-Formyl-benzoic acid ethyl ester | 120° C./2 hr | 92 |
| 10 | 4-Dibromomethyl-biphenyl | Biphenyl-4-carbaldehyde | 100° C./2 hr | 97 |
| 11 | Dichloromethyl-benzene | Benzaldehyde | 100° C./2 hr | 95 |
| 12 | 1-Dichloromethyl-2-fluoro-benzene | 2-Fluoro-benzaldehyde | 120° C./18 hr | 98 |
| 13 | 1-Dichloromethyl-3-fluoro-benzene | 3-Fluoro-benzaldehyde | 100° C./10 hr | 93 |

In another preferred embodiment of the present invention, DMSO reacted with a substituted or unsubstituted 2-(dihalomethyl) indole compound, most preferably a 2-(dichloromethyl)- or 2-(dibromomethyl)-indole compound, at room temperature (about 15–35° C.). This embodiment is illustrated below in Method A, and in Examples 1 and 42 below. The indole may be substituted with any substituents set forth in the definition of formula (I) or in the examples below.

The reaction of the present invention may be used as part of a process for making compounds of the formula:

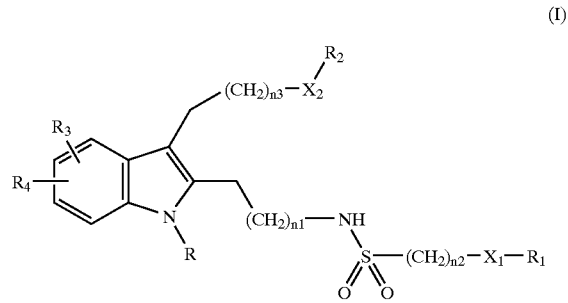

(I)

wherein:

R is selected from the formulae —$(CH_2)_n$-A, —$(CH_2)_n$—S-A, or —$(CH_2)_n$—O-A, wherein A is selected from the moieties:

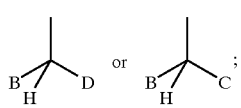

wherein

D is $C_1$–$C_6$ lower alkyl, $C_1$–$C_6$ lower alkoxy, $C_3$–$C_6$ cycloaklyl —$CF_3$ or —$(CH_2)_{1-3}$—$CF_3$;

B and C are independently selected from phenyl, pyridinyl, pyrimidinyl, furanyl, thiophenyl or pyrrolyl groups, each optionally substituted by from 1 to 3, preferably 1 to 2, substituents selected independently from H, halogen, —CN, —CHO, —$CF_3$, —$OCF_3$, —OH, —$C_1$–$C_6$ alkyl, $C_1$–$C_6$ alkoxy, —$NH_2$, —N($C_1$–$C_6$)$_2$, —NH($C_1$–$C_6$), —N—C(O) —($C_1$–$C_6$), —$NO_2$, or by a 5- or 6-membered heterocyclic or heteroaromatic ring containing 1 or 2 heteroatoms selected from O, N or S; or n is an integer from 0 to 3;

$n_1$ is an integer from 1 to 3;

$n_2$ is an integer from 0 to 4;

$n_3$ is an integer from 0 to 3;

$n_4$ is an integer from 0 to 2;

$X_1$ is selected from a chemical bond, —S—, —O—, —S(O)—, —S(O)$_2$—, —NH—, —NHC(O)—, —C=C—,

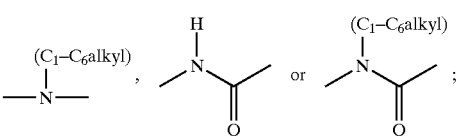

$R_1$ is a moiety selected from $C_1$–$C_6$ alkyl, $C_1$–$C_6$ fluorinated alkyl, $C_3$–$C_6$ cycloalkyl, tetrahydropyranyl, camphoryl, adamantyl, CN, —N($C_1$–$C_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7, dimethylbicyclo[2.2.1]heptan-2-one, Benzo[1,2,5]oxadiazole, 2-Oxa-5-aza-bicyclo[2.2.1]heptane, Piperazin-2-one or pyrrolyl groups, each optionally substituted by from 1 to 3, preferably 1 to 2, substituents independently selected from H, halogen, —CN, —CHO, —$CF_3$, $OCF_3$, —OH, —$C_1$–$C_6$ alkyl, $C_1$–$C_6$ alkoxy, —$NH_2$, —N($C_1$–$C_6$)$_2$, —NH ($C_1$–$C_6$), —N—C(O)—($C_1$–$C_6$), —$NO_2$, —$SO_2$($C_1$–$C_3$ alkyl), —$SO_2NH_2$, —$SO_2NH$($C_1$–$C_3$ alkyl), —$SO_2N$($C_1$–$C_3$ alkyl)$_2$, —COOH, —$CH_2$—COOH, —$CH_2$—N($C_1$–$C_6$ alkyl), —$CH_2$—N($C_1$–$C_6$ alkyl)$_2$, —$CH_2$—$NH_2$, pyridine, 2-Methyl-thiazole, morpholino, 1-Chloro-2-methyl-propyl, —$C_1$–$C_6$ thioalkyl, phenyl (further optionally substituted with halogens), benzyloxy, ($C_1$–$C_3$ alkyl)C(O)$CH_3$, ($C_1$–$C_3$ alkyl)$OCH_3$, C(O)$NH_2$, or

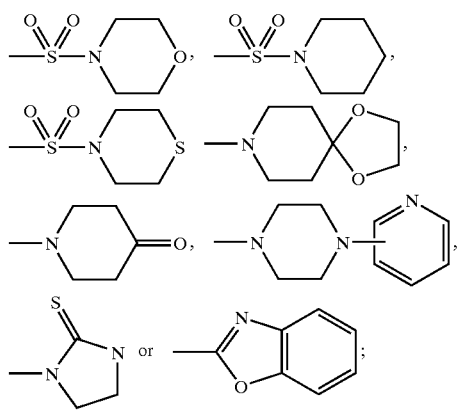

$X_2$ is selected from —O—, —$CH_2$—, —S—, —SO—, —$SO_2$—, —NH—, —C(O)—,

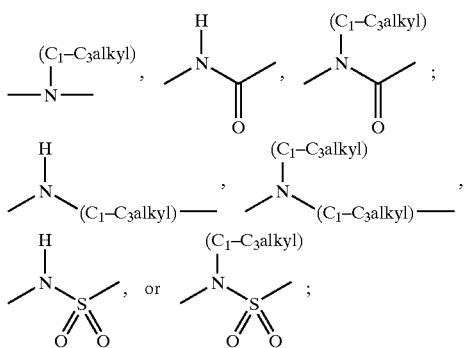

R$_2$ is a ring moiety selected from phenyl, pyridinyl, pyrimidinyl, furyl, thienyl or purrolyl groups, the ring moiety being substituted by a group of the formula —(CH$_2$)$_{n4}$—CO$_2$H or a pharmaceutically acceptable acid mimic or mimetic; and also optionally substituted by 1 or 2 additional substituents independtly selected from H, halogen, —CN, —CHO, —CF$_3$, —OCF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), or —NO$_2$;

R$_3$ is selected from H, halogen, —CN, —CHO, —CF$_3$, —OCF$_3$, —OH, —C$_1$–C$_6$ alkyl, C$_1$–C$_6$ alkoxy, C$_1$–C$_6$ thioalkyl, —NH$_2$, —N(C$_1$–C$_6$), —NH(C$_1$–C$_6$), —N—C(O)—C$_1$–C$_6$), or —NO$_2$;

R$_4$ is selected from H, halogen, —CN, —CHO, —CF$_3$, —OCF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), —NO$_2$, —N—C(O)—N(C$_1$–C$_3$ alkyl)$_2$, —N—C(O)—NH(C$_1$–C$_3$ alkyl), —N—C(O)—O—(C$_1$–C$_3$ alkyl), —SO$_2$—C$_1$–C$_6$ alkyl, —S—C$_3$–C$_6$ cycloalkyl, —S—CH$_2$–C$_3$–C$_6$ cycloalkyl, —SO$_2$—C$_3$–C$_6$ cycloalkyl, —SO$_2$—O—CH$_2$—C$_3$–C$_6$ cycloalkyl, phenyl, benzyl, benzyloxy, morpholino or other heterocycles such as pyrrolidino, piperidine, piperizine furan, thiophene, imidazole, tetrazole, pyrazine, pyrazolone, pyrazole, imidazole, oxazole or isoxazole, the rings of each of these R$_4$ groups each being optionally substituted by from 1 to 3 substituents selected from the group of H, halogen, —CN, —CHO, —CF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), —NO$_2$, —SO$_2$(C$_1$–C$_3$ alkyl), —SO$_2$NH(C$_1$–C$_3$ alkyl), —SO$_2$N(C$_1$–C$_3$ alkyl)$_2$, or OCF$_3$;

or a pharmaceutically acceptable salt form thereof.

Preferred R$_2$ groups include phenyl having a substituent —(CH$_2$)$_{n4}$COOH or —(CH$_2$)$_{n4}$COOR$_{10}$, where R$_{10}$ is a C$_1$–C$_6$ alkyl group and n$_4$ is an integer from 0 to 2, particularly where this substitution is at the 4-position.

It will be understood that the C$_1$–C$_6$ fluorinated alkyl groups in the definition of R$_1$ may be any alkyl group of 1 to 6 carbon atoms with any amount of fluorine substitution including, but not limited to, —CF$_3$, alkyl chains of 1 to 6 carbon atoms terminated by a trifluoromethyl group, —CF$_2$CF$_3$, etc.

Ester forms of the present compounds include the pharmaceutically acceptable ester forms known in the art including those which can be metabolized into the free acid form, such as a free carboxylic acid form, in the animal body, such as the corresponding alkyl esters, cycloalkyl esters, aryl esters and heterocyclic analogues thereof can be used according to the invention, where alkyl esters, cycloalkyl esters and aryl esters are preferred and the alcoholic residue can carry further substituents. C$_1$–C$_8$ alkyl esters, preferably C$_1$–C$_6$ alkyl esters, such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester are particularly preferred.

In the definition of X$_1$, the alkenyl bridging group —C=C— is understood to indicate either the cis or trans orientation of the indicated compound(s).

Pharmaceutically acceptable acid mimics or mimetics useful in the compounds of this invention include those wherein R$_2$ is selected from the group of:

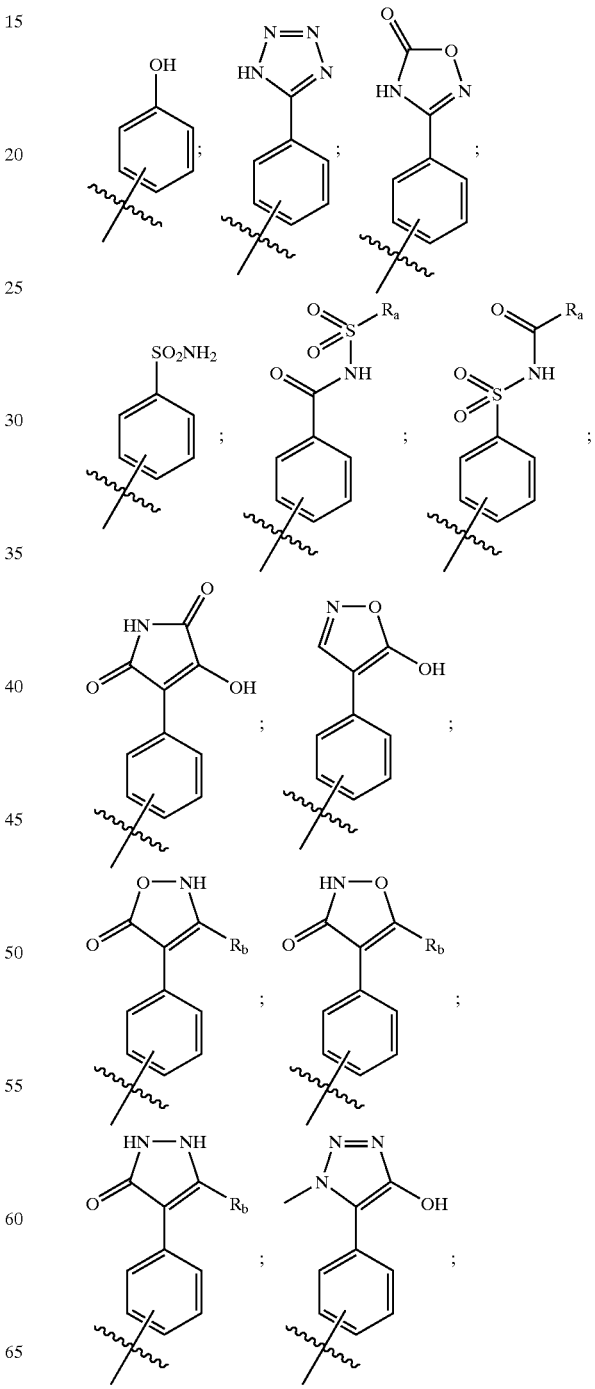

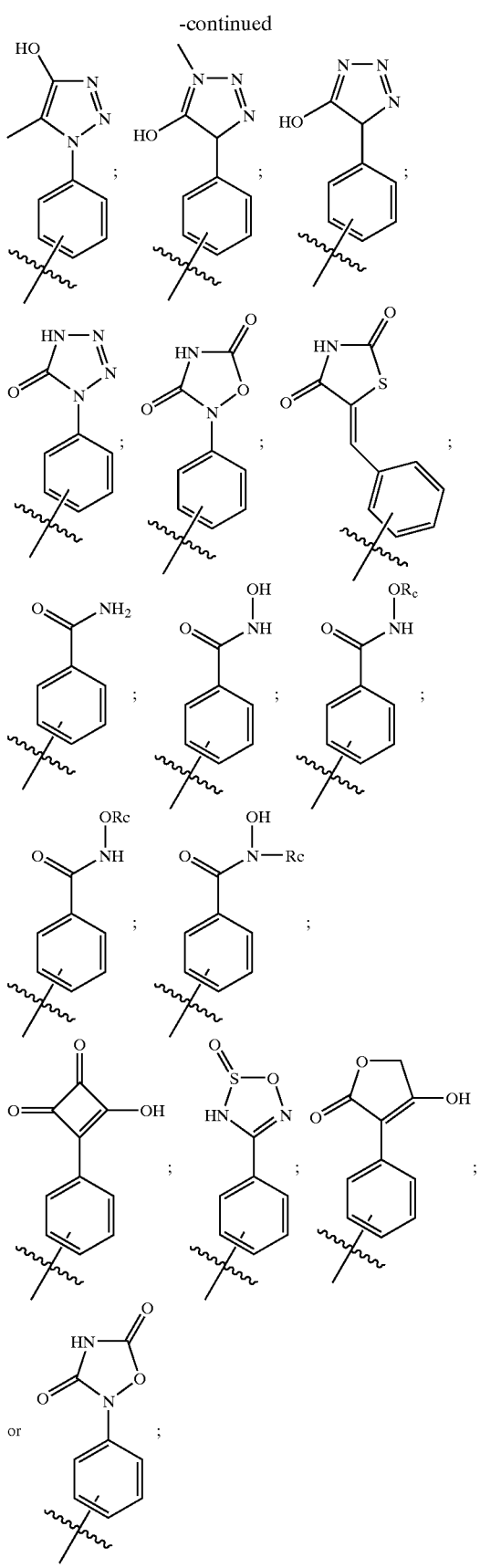

wherein $R_a$ is selected from —$CF_3$, —$CH_3$, phenyl, or benzyl, with the phenyl or benzyl groups being optionally substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; $R_b$ is selected from —$CF_3$, —$CH_3$, —$NH_2$, phenyl, or benzyl, with the phenyl or benzyl groups being optionally substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; and $R_c$ is selected from —$CF_3$ or $C_1$–$C_6$ alkyl.

A first subgroup of compounds of this invention, or a pharmaceutically acceptable salt thereof, include those of the group above wherein A is the moiety:

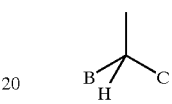

and B, C, n, n1, n2, n3, n4, R, $X_1$, $X_2$, $R_1$, $R_2$, $R_3$, and $R_4$ are as defined above.

A second subgroup of compounds of this invention comprises those of the first subgroup, above, wherein B and C are unsubstituted phenyl, pyridinyl, pyrimidinyl, furyl, thienyl or pyrrolyl groups and R, B, C, n, n1, n2, n3, n4, $R_1$, $X_1$, $X_2$, $R_2$, $R_3$, and $R_4$ are as defined above.

A third subgroup of compounds and pharmaceutically acceptable salt forms of this invention comprise those of the second subgroup, above, wherein A is the moiety:

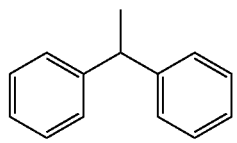

and n, n1, n2, n3, n4, R, $X_1$, $X_2$, $R_1$, $R_2$, $R_3$, and $R_4$ are as defined above.

A fourth subgroup of compounds of this invention comprises those of the formulae (II) or (III):

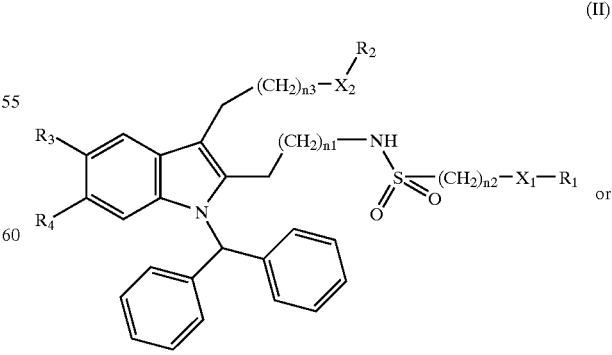

(II)

or

-continued (III)

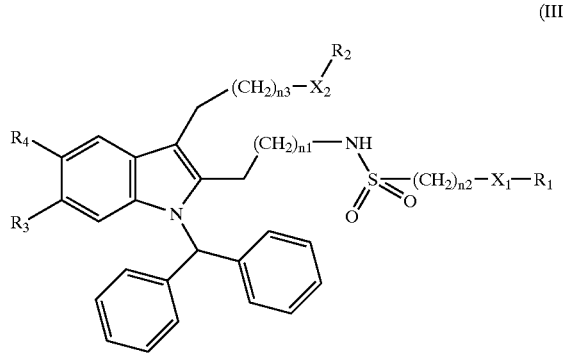

wherein n1, n2, n3, n4, $X_1$, $X_2$, $R_1$, $R_2$, $R_3$, and $R_4$ are as defined above, or a pharmaceutically acceptable salt thereof.

A fifth subgroup of compounds of this invention includes those of formulae (II) or (III) wherein n3=1, and n1, n2, n4, $X_1$, $X_2$, $R_1$, $R_2$, $R_3$, and $R_4$ are as defined above, or a pharmaceutically acceptable salt thereof.

A sixth subgroup of compounds of this invention includes those of the fifth subgroup, above, wherein $R_2$ is phenyl substituted by a group of the formula —$(CH_2)_{n4}$—$CO_2H$; and optionally substituted by 1 or 2 additional substituents independently selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —$N(C_1$-$C_6)_2$, —$NH(C_1$-$C_6)$, —N—C(O)—$(C_1$-$C_6)$, or —NO; and n1, n2, n4, $R_1$, $X_1$, $X_2$, $R_2$, $R_3$, and $R_4$ are as defined above, or a pharmaceutically acceptable salt thereof.

A seventh subgroup of compounds of this invention comprises those of the formula (IV):

(IV)

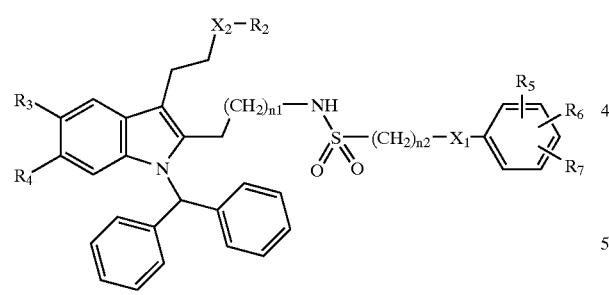

wherein:
$n_1$ is an integer from 1 to 3;
$n_2$ is an integer from 1 to 3;
$R_5$, $R_6$ and $R_7$ are independently selected from H, halogen, —CN, —CHO, —$CF_3$, —$OCF_3$, —OH, —$C_1$-$C_6$ alkyl, $C_1$-$C_6$ alkoxy, —$NH_2$, —$N(C_1$-$C_6)_2$, —$NH(C_1$-$C_6)$, —N—C(O)—$(C_1$-$C_6)$, or —$NO_2$;
$X_1$ is selected from a chemical bond, —S—, —O—, —NH— or —N($C_1$-$C_3$ alkyl)-;
$X_2$ is selected from —O—, —$SO_2$— or —$CH_2$—;
$R_2$ is a moiety selected from the group of:

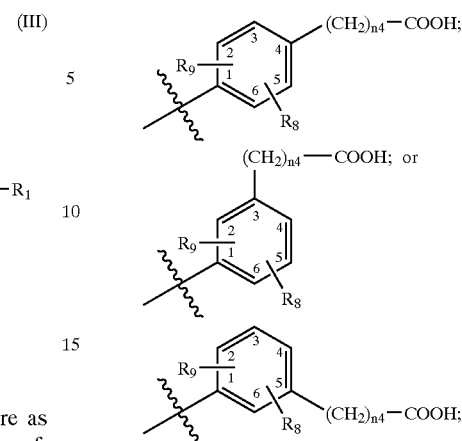

$R_8$ and $R_9$ are independently selected from H, halogen, —CN, —CHO, —$CF_3$, —OH, —$C_1$-$C_6$ alkyl, $C_1$-$C_6$ alkoxy, —$NH_2$, —$N(C_1$-$C_6)_2$, —$NH(C_1$-$C_6)$, —N—C(O)—$(C_1$-$C_6)$, or —$NO_2$;

$n_4$ is an integer from 0 to 2;

$R_3$ is selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —$N(C_1$-$C_6)_2$, —$NH(C_1$-$C_6)$, —N—C(O)—$(C_1$-$C_6)$, or —$NO_2$; and $R_4$ is selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —$N(C_1$-$C_6)_2$, —$NH(C_1$-$C_6)$, —N—C(O)—$(C_1$-$C_6)$, —$NO_2$, morpholino or other heterocycles such as pyrrolidino, piperidine, piperizine, furan, thiophene, imidazole, tetrazole, pyrazine, pyrazolone, pyrazole, imidazole, oxazole or isoxazole;

or a pharmaceutically acceptable salt form thereof.

An eighth subgroup of compounds of this invention include those of the formulae (VI) or (VII):

(VI)

(VII)

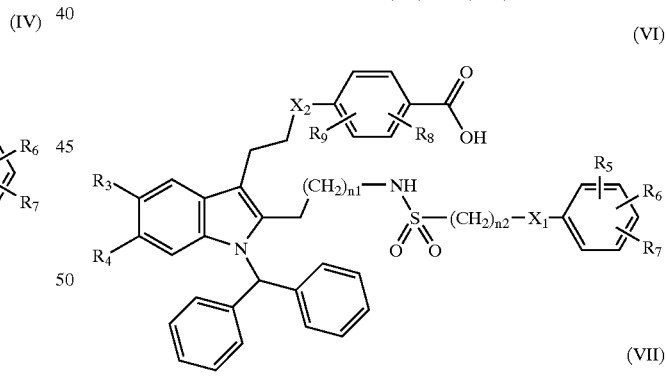

wherein:

$X_1$ is selected from a chemical bond, —S—, —O—, —NH— or —N($C_1$-$C_3$ alkyl)-;

$X_2$ is selected from —O—, —$SO_2$—, or —$CH_2$—;

$R_3$ is selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —N($C_1$-$C_6$)$_2$, —NH($C_1$-$C_6$), —N—C(O)—($C_1$-$C_6$), or —$NO_2$; and $R_4$ is selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —N($C_1$-$C_6$)$_2$, —NH($C_1$-$C_6$), —N—C(O)—($C_1$-$C_6$), —$NO_2$, morpholino or other heterocycles such as pyrrolidino, piperidine, piperizine, furan, thiophene, imidazole, tetrazole, pyrazine, pyrazolone, pyrazole, imidazole, oxazole or isoxazole;

$n_1$ is an integer from 1 to 2;

$n_2$ is an integer from 1 to 2;

$R_5$, $R_6$ and $R_7$ are independently selected from H, halogen, —CN, —CHO, —$CF_3$, —$OCF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), or —$NO_2$;

$R_8$ and $R_9$ are independently selected from H, halogen, —CN, —CHO, —$CF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), or —$NO_2$;

or a pharmaceutically acceptable salt form thereof.

A ninth subgroup of compounds of this invention include those of formulae (VI) or (VII) wherein: $n_1$ is 1; $n_2$ is 1; and $X_1$, $X_2$, $R_3$, $R_4$, $R_5$, $R_6$, $R_7$, $R_8$ and $R_9$ are as defined in the eighth subgroup, above, or a pharmaceutically acceptable salt form thereof.

A tenth subgroup of this invention comprises the compounds of the ninth subgroup, above, wherein $X_1$ is a chemical bond and $n_1$, $n_2$, $X_2$, $R_3$, $R_4$, $R_5$, $R_6$, $R_7$, $R_8$ and $R_9$ are as defined in the ninth subgroup, above, or a pharmaceutically acceptable salt form thereof.

An eleventh subgroup of compounds of this invention comprises those of the formula (VIII)

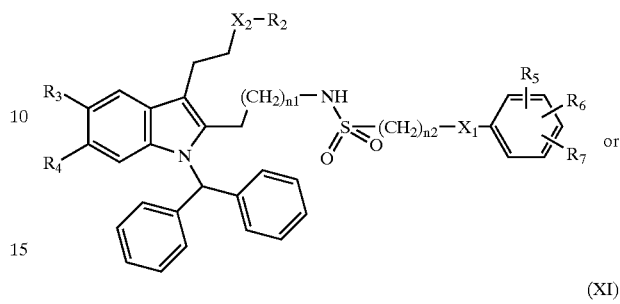
(VIII)

wherein:

$n_1$ is an integer from 1 to 3;

$n_2$ is 0;

$X_1$ is a chemical bond;

n3, n4, $X_2$, $R_1$, $R_2$, $R_3$, and $R_4$ are as defined above, or a pharmaceutically acceptable salt thereof.

A twelfth subgroup of compounds of this invention comprises those of the formulae (X) or (XI)

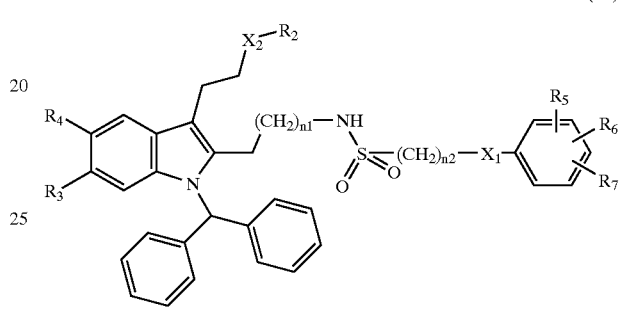
(X)

(XI)

wherein:

$n_1$ is an integer from 1 to 3;

$n_2$ is 0;

$R_5$, $R_6$ and $R_7$ are independently selected from H, halogen, —CN, —CHO, —$CF_3$, —$OCF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), or —$NO_2$;

$X_1$ is a chemical bond $X_2$ is selected from —O—, —$SO_2$—, or —$CH_2$—;

$R_2$ is a moiety selected from the group of:

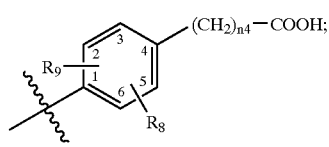

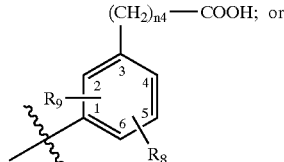

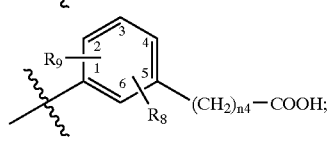

$R_8$ and $R_9$ are independently selected from H, halogen, —CN, —CHO, —$CF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), or —$NO_2$;

$n_4$ is an integer from 0 to 2;

$R_3$ is selected from H, halogen, —CN, —CHO, —CF$_3$, —OH, —C$_1$-C$_6$ alkyl, C$_1$-C$_6$ alkoxy, C$_1$-C$_6$ thioalkyl, —NH$_2$, —N(C$_1$-C$_6$)$_2$, —NH(C$_1$-C$_6$), —N—C(O)—(C$_1$-C$_6$), or —NO$_2$; and $R_4$ is selected from H, halogen, —CN, —CHO, —CF$_3$, —OH, —C$_1$-C$_6$ alkyl, C$_1$-C$_6$ alkoxy, C$_1$-C$_6$ thioalkyl, —NH$_2$, —N(C$_1$-C$_6$)$_2$, —NH(C$_1$-C$_6$), —N—C(O)—(C$_1$-C$_6$), —NO$_2$, morpholino or other heterocycles such as pyrrolidino, piperidine, piperizine, furan, thiophene, imidazole, tetrazole, pyrazine, pyrazolone, pyrazole, imidazole, oxazole or isoxazole;

or a pharmaceutically acceptable salt form thereof.

A thirteenth subgroup of compounds of this invention include those of the formulae (XII) or (XIII):

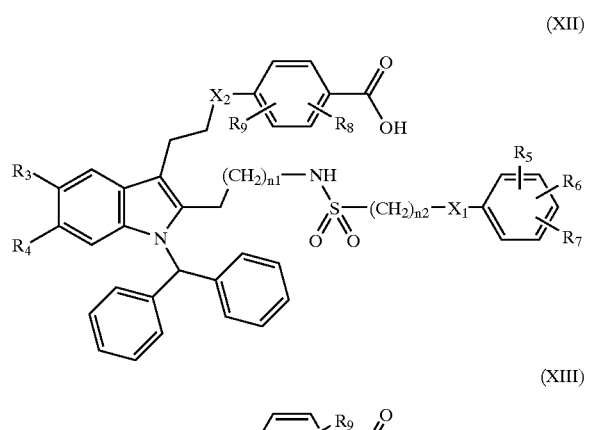

(XII)

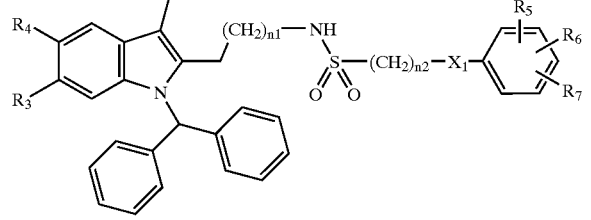

(XIII)

wherein:
X$_1$ is a chemical bond;
X$_2$ is selected from —O—, —SO$_2$—, or —CH$_2$;
R$_3$ is selected from H, halogen, —CN, —CHO, —CF$_3$, —OH, —C$_1$-C$_6$ alkyl, C$_1$-C$_6$ alkoxy, C$_1$-C$_6$ thioalkyl, —NH$_2$, —N(C$_1$-C$_6$)$_2$, —NH(C$_1$-C$_6$), —N—C(O)—(C$_1$-C$_6$), or —NO$_2$; and
R$_4$ is selected from H, halogen, —CN, —CHO, —CF$_3$, —OH, —C$_1$-C$_6$ alkyl, C$_1$-C$_6$ alkoxy, C$_1$-C$_6$ thioalkyl, —NH$_2$, —N(C$_1$-C$_6$)$_2$, —NH(C$_1$-C$_6$), —N—C(O)—(C$_1$-C$_6$), —NO$_2$, morpholino or other heterocycles such as pyrrolidino, piperidine, piperizine, furan, thiophene, imidazole, tetrazole, pyrazine, pyrazolone, pyrazole, imidazole, oxazole or isoxazole;
n$_1$ is an integer from 1 to 2;
n$_2$ is 0;
R$_5$, R$_6$ and R$_7$ are independently selected from H, halogen, —CN, —CHO, —CF$_3$, —OCF$_3$, —OH, —C$_1$-C$_6$ alkyl, C$_1$-C$_6$ alkoxy, —NH$_2$, —N(C$_1$-C$_6$)$_2$, —NH(C$_1$-C$_6$), —N—C(O)—(C$_1$-C$_6$), or —NO$_2$;
R$_8$ and R$_9$ are independently selected from H, halogen, —CN, —CHO, —CF$_3$, —OH, —C$_1$-C$_6$ alkyl, C$_1$-C$_6$ alkoxy, —NH$_2$, —N(C$_1$-C$_6$)$_2$, —NH(C$_1$-C$_6$), —N—C(O)—(C$_1$-C$_6$), or —NO$_2$;
or a pharmaceutically acceptable salt form thereof.

The compounds of formula (I) inhibit cPLA2 activity that is required for supplying arachidonic acid substrate to cyclooxygenase-1 or 2 and 5-lipoxygenase, which in turn initiate the production of prostaglandins and leukotrienes respectively. In addition, cPLA2 activity is essential for producing the lyso-phospholipid that is the precursor to PAF. Thus these compounds are useful in the treatment and prevention of disease states in which leukotrienes, prostaglandins or PAF are involved. Moreover, in diseases where more than one of these agents plays a role, a cPLA2 inhibitor would be expected to be more efficacious than leukotriene, prostaglandin or PAF receptor antagonists and also more effective than cyclooxygenase or 5-lipoxygenase inhibitors.

These compounds will be especially useful in the treatment of arthritic and/or rheumatic disorders, including but not limited to rheumatoid arthritis, spondylo-arthropathies, gouty arthritis, osteoarthritis, systemic lupus erythematosus and juvenile arthritis. The compounds of this invention will be useful in the treatment of post-operative inflammation including that following ophthalmic surgery such as cataract surgery or refractive surgery.

This invention can be further understood by the following non-limiting specific examples.

Method A

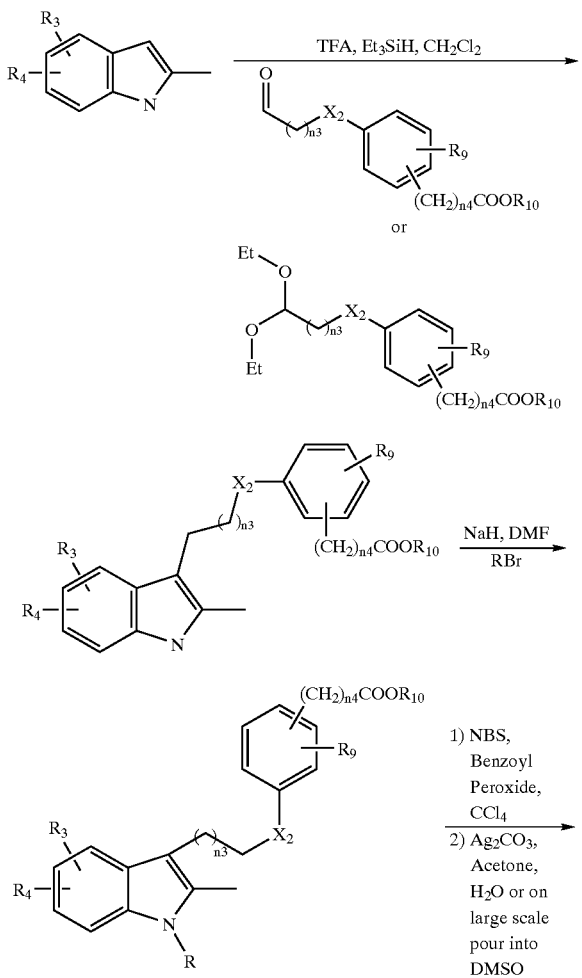

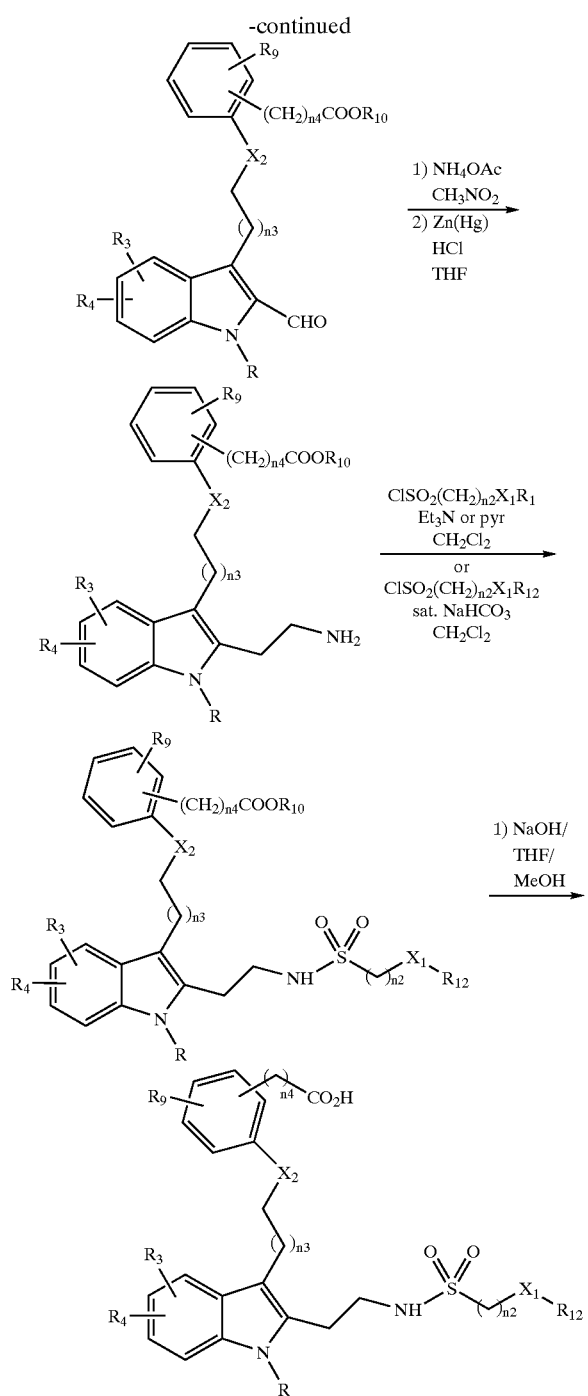

Method A

The initial indole of Method A may be alkylated at the C3 position (the carbon atom at the 3-position of the indole moiety) with aldehydes or the corresponding acetals in the presence of a Lewis or Bronsted acid, such as boron triflouride etherate or trifluoroacetic acid. The indole nitrogen may then be alkylated by treatment with a strong base such as sodium bis(trimethylsilyl) amide, n-BuLi, sodium hydride or potassium hydride in a solvent such as DMF, DMSO or THF followed by exposure to the appropriate alkyl halide. The resulting product can be treated with carbon tetrabromide in carbon tetrachloride and a catalytic amount of benzoyl peroxide to effect dibromination of the C2 methyl group. The dibromide can then either be stirred with silver carbonate in acetone water or poured into DMSO and stirred. Both of these procedures generate the aldehyde which is then subjected to the nitro aldol reaction with nitromethane and a catalytic amount of ammonium acetate at reflux. The resulting vinyl nitro intermediate is reduced to the amine upon treatment with zinc mercury amalgam in a mixture of THF and conc. HCL at reflux. This amine can then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.). This method was used in the synthesis of Examples 1–88.

Method B

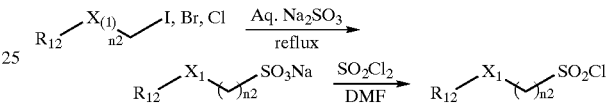

The initial halide of Method B is refluxed in aqueous sodium sulfite and a suitable cosolvent if necessary, such as alcohol, dioxane etc, for the required amount of time to form the desired sodium sulfonate. This intermediate was treated with thionyl chloride, phosphorous pentachloride or oxalyl chloride, in dichloromethane with a small amount of DMF and stirred for several hours at room temperature until the sulfonyl chloride is formed. The thus formed sulfonyl chloride is then used crude in Method A. This method was used in the synthesis of Examples 1–88 when the sulfonyl chloride was not commercially available.

EXAMPLE 1

4-[2-(1-Benzhydryl-2-{2-[(benzylsulfonyl)amino]ethyl}-5-chloro-1H-indol-3-yl)ethoxy]benzoic acid This synthesis is depicted in Method A.

Step 1: To 4-hydroxy-benzoic acid methyl ester (1.0 eq) in DMF (0.83 M) was added $K_2CO_3$ (2.0 eq) followed by 2-bromo-1,1-diethoxy-ethane and the reaction mixture was stirred at 110° C. for 2 days. TLC showed a new spot. The reaction mixture was diluted with ethyl acetate, washed with 1N NaOH, water, and brine, dried over sodium sulfate, and solvent was removed to afford desired product in 84% yield. This material was used in the next step without further purification.

Step 2: To the above product (1.0 eq) and 5-chloro-2-methyl indole (1.0 eq) in $CH_2Cl_2$ (0.12 M) was added triethylsilane (3.0 eq) followed by trifluoroacetic acid (3.0 eq). After being stirred overnight at room temperature, added water and trifluroacetic acid (1.0 eq) to the reaction mixture, stirred at room temperature for two days, diluted with $CH_2Cl_2$, washed with 1N NaOH, water, brine, dried over sodium sulfate. Trituration of the material with $CH_2Cl_2$ and hexanes afforded the C3 alkylated indole in 92% yield Step 3: To the indole from above (1.0 eq) in DMF (0.36 M) at 25° C. was added NaH (1.2 eq, 60% dispersion in oil), and the brown solution was stirred at 0 to –5° C. for 1 h and then compound bromodiphenylmethane was added (1.1 eq), and then the reaction mixture was stirred overnight. It was then quenched with water, diluted with ethyl acetate, washed with water and brine, dried over sodium sulfate and purified by column chromatography to yield 72% of the desired product.

Step 4: To the N-alkylated indole from above (1.0 eq) in $CCl_4$ (0.2 M) was added N-bromosuccinimide (2.0 eq) and a catalytic amount of benzoyl peroxide. The solution was heated to reflux for 3 h, cooled to 25° C., filtered, and the solid was washed with $CCl_4$. The filtrate was concentrated to a foam, which was dried. The foam was dissolved in acetone, and $Ag_2CO_3$ (1.1 eq.) was added followed by water and the reaction mixture was stirred overnight at room temperature. It was filtered and washed with acetone. The filtrate was concentrated to a residue, to which was added water. This mixture was extracted with ethyl acetate, washed with brine, dried over sodium sulfate and then chromatographic purification on the residue gave the desired product in 85% yield. Alternatively the dibromide from the reaction with NBS could be poured into DMSO (10–20% concentration by weight) stirred for 30 minutes at room temperature. When the reaction was deemed complete it was poured into water and the resulting precipitate was isolated by filtration, the cake was washed with water and dried to yield an essentially quantitative yield.

Step 5: To the above aldehyde (1.0 equiv) in $CH_3NO_2$ (0.2 M) was added ammonium acetate (4 equiv) and the resulting mixture was heated to reflux for 4 h. The reaction mixture was then diluted with EtOAc and washed with brine. The aqueous phase was extracted with EtOAc. The combined organic extracts were washed with brine, dried over sodium sulfate, and concentrated until an orange crystalline solid precipitated. The mixture was refrigerated overnight and the nitroolefin (76% yield) was collected by filtration. Evaporation of the solution phase and purification of the residue by column chromatography (gradient elution 100% toluene→1% EtOAc-toluene) afforded an additional amount of the nitroolefin (23% yield).

Step 6: Zinc dust (20 equiv) was suspended in 5% aqueous HCl solution (8 M Zn/5% HCl). To this mixture was added $HgCl_2$ (0.28 equiv). The mixture was shaken for 10 min, the aqueous phase was decanted and replaced with fresh 5% HCl, and again the mixture was shaken for 5 min and the aqueous phase was removed. The zinc-mercury amalgam thus generated was then added to a mixture of the nitroolefin (1.0 equiv) and conc. HCl (80 equiv) in THF (0.04 M nitroolefin/THF). The mixture was maintained at a gentle reflux for 1 h. The formation of product was followed by TLC analysis. The mixture was cooled to room temperature and the solids were removed by filtration through Celite. Conc. $NH_4OH$ was added to the solution phase and the mixture was concentrated on the rotary evaporator. The residue was dissolved in $CH_2Cl_2$ and conc. $NH_4OH$. The aqueous phase was extracted with $CH_2Cl_2$, and the organic phase was washed with brine, dried over sodium sulfate, and concentrated. Purification by column chromatography afforded the desired product (65% yield).

Step 7: To methyl 4-{2-[2-(2-aminoethyl)-1-benzhydryl-5-chloro-1H-indol-3-yl] ethoxy}benzoate (1.0 equiv) and sat. $NaHCO_3$ (0.14 M) in $CH_2Cl_2$ (0.07 M) was added α-toluenesulfonyl chloride (1.0 equiv). After 1 h the mixture was poured into saturated sodium bicarbonate and extracted with $CH_2Cl_2$. The combined organic phase was washed with brine, dried over sodium sulfate and purified by column chromatography (gradient elution using 20% EtOAc-hexanes→50% EtOAc-hexanes) to afford 86% of the desired product.

Step 8: The resulting ester was hydrolyzed by stirring with 1N NaOH (5 equiv) in THF (0.07 M) and enough MeOH to produce a clear solution. The reaction was monitored by TLC (10% MeOH—$CH_2Cl_2$) for the disappearance of starting material. The mixture was heated in a 60 degrees C. oil bath for 2 hour. The mixture was concentrated, diluted with $H_2O$, and acidified to pH 2–4 using 1 M HCl. The aqueous phase was extracted with EtOAc and the organic phase was washed with brine, dried over sodium sulfate, and concentrated to afford the desired product in 92% yield. HRMS calc for $[C_{39}H_{35}ClN_2O_5.S+H]$ 679.2028 found 679.2031.

EXAMPLE 2

4-[2-(1-Benzhydryl-5-chloro-2-{2-[(isopropylsulfonyl)-amino] ethyl}-1H-indol-3-yl) thoxy]benzoic acid Step 1: This compound was prepared from methyl 4-{2-[2-(2-aminoethyl)-1-benzhydryl-5-chloro-1H-indol-3-yl] ethoxy}benzoate (Step 6, Example 1) and isopropylsulfonyl chloride according to the procedure in Example 1 Step 7 in 55% yield.

Step 2: The ester intermediate was hydrolyzed according to Step 8 Example 1 to afford the title acid in 81% yield. HRMS calc for $[C_{35}H_{35}ClN_2O_5.S+H]$ 631.2028 found 631.2029.

EXAMPLE 3

4-[2-(1-Benzhydryl-2-{2-[(butylsulfonyl)amino] ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl] ethoxy}benzoate (Step 6, Example 1) and 1-butanesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{36}H_{37}ClN_2O_5.S+H]$ 645.2185 found 645.2185.

EXAMPLE 4

4-{2-[1-Benzhydryl-5-chloro-2-(2-{[(1-methyl-1H-imidazol-4-yl)sulfonyl] amino}ethyl)-1H-indol-3-yl] ethoxy}benzoic acid Step 1: To methyl 4-{2-[2-(2-aminoethyl)-1-benzhydryl-5-chloro-1H-indol-3-yl] ethoxy}benzoate (Step 6, Example 1) (1.0 equiv) and $Et_3N$ (3.0 equiv) or pyridine (3.0 equiv) in $CH_2Cl_2$ (0.05 M) was added 1-methylimidazole-4-sulfonyl chloride (1.2 equiv). The reaction was monitored by TLC (10% MeOH—$CH_2Cl_2$) and was heated if necessary. After 30 min the mixture was poured into saturated sodium bicarbonate and extracted with $CH_2Cl_2$. The combined organic phase was washed with brine, dried over sodium sulfate and purified by column chromatography to afford 92% of the desired product.

Step 2: The ester intermediate was hydrolyzed according to Step 8 Example 1 to afford the title acid in 89% yield. HRMS calc for $[C_{36}H_{33}ClN_4O_5.S+H]$ 669.1933 found 669.1932.

EXAMPLE 5

4-{2-[1-Benzhydryl-2-(2-{[(5-bromo-6-chloro-3-pyridinyl)sulfnyl] amino}ethyl)-5-chloro-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 3-bromo-2-chloropyridine-5-sulfonyl chloride according to the procedure in Example 1 Step 7 in 74% yield.

Step 2: The ester intermediate was hydrolyzed according to Step 8 Example 1 to afford the title acid in 98% yield. HRMS calc for $[C_{37}H_{30}BrCl_2N_3O_5.S+H]$ 778.0539 found 778.0544.

EXAMPLE 6

4-[2-(1-Benzhydryl-5-chloro-2-{2-[({[(1R)-7,7-dimethyl-2-oxobicyclo[2.2.1hept-1-yl]methyl}sulfonyl)amino]ethyl}-1H-indol-3-yl)ethoxy] benzoic acid Step 1: This compound was prepared from methyl 4-{2-[2-(2-aminoethyl)-1-benzhydryl-5-chloro-1H-indol-3-yl]ethoxy}benzoate (Step6, Example 1) and (1R)-(−)-10-camphorsulfonyl chloride according to the procedure in Example 1 Step 7 in 77% yield.

Step 2: The ester intermediate was hydrolyzed according to Step 8 Example 1 to afford the title acid in 94% yield. HRMS calc for $[C_{42}H_{43}ClN_2O_6.S+H]$ 739.2603 found 739.26.

EXAMPLE 7

4-(2-{1-Benzhydryl-5-chloro-2-[2-({[(methylsulfonyl)methyl]sulfonyl}amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step6, Example 1) and (methanesulfonyl)methanesulfonyl chloride according to the procedure in Example 4 Step 1 in 43% yield.

Step 2: The ester intermediate was hydrolyzed according to Example 117 Step 2 to afford the title acid in 95% yield. HRMS calc for $[C_{34}H_{33}ClN_2O_7.S_2+H]$ 681.1491 found 681.1489.

EXAMPLE 8

4-(2-{1-Benzhydryl-5-chl ro-2-[2-({[(2-(1-naphthyl)ethyl] sulfonyl}amino)ehtyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step6, Example 1) and 2-(1-naphthyl)ethanesulfonyl chloride according to the procedure Example 1 Step 7 in 60% yield.

Step 2: The ester intermediate was hydrolyzed according to Step 8 Example 1 to afford the title acid in 100% yield. HRMS calc for $[C_{44}H_{39}ClN_2O_5.S+H]$ 743.2341 found 743.2338.

EXAMPLE 9

4-{2-[1-Benzhydryl-5-chloro-2-{2-[({2-nitrobenzyl}-sulfonyl)amino] ethyl}-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step6, Example 1) and 2-nitro-α-toluenesulfonyl chloride according to the procedure in Example 1 Step 7 in 82% yield.

Step 2: The ester intermediate was hydrolyzed according to Step 8 Example 1 to afford the title acid in 85% yield. HRMS calc for $[C_{39}H_{34}ClN_3O_7.S+H]$ 724.1879 found 724.1877.

EXAMPLE 10

4-{2-[1-Benzhydryl-5-chloro-2-(2-{[(3,4-dichlorobenzyl)sulfonyl] amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step6, Example 1) and [(3,4-dichlorophenyl)-methyl] sulfonyl chloride according to the procedure in Example 1 Step 7 in 82% yield.

Step 2: The ester intermediate was hydrolyzed according to Step 8 Example 1 to afford the title acid in 86% yield. HRMS calc for $[C_{39}H_{33}Cl_3N_2O_5.S+H]$ 747.1249 found 747.1249.

EXAMPLE 11

4-{2-[1-Benzhydryl-5-chloro-2-(2-{[(3,5-dichlorobenzyl)sulfonyl] amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step6, Example 1) and [(3,5-dichlorophenyl)-methyl] sulfonyl chloride according to the procedure in Example 1 Step 7 in 100% yield.

Step 2: The ester intermediate was hydrolyzed according to Step 8 Example 1 to afford the title acid in 98% yield. HRMS calc for $[C_{39}H_{33}Cl_3N_2O_5.S+H]$ 747.1249 found 747.1249.

EXAMPLE 12

4-(2-}1-Benzhydryl-5-chloro-2-(2-({[(3-(trifluoromethyl)-benzyl] sulfonyl}-amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step6, Example 1) and [[3-(trifluoromethyl)-phenyl] methyl]sulfonyl chloride according to the procedure in Example 1 Step 7 in 74% yield.

Step 2: The ester intermediate was hydrolyzed according to Step 8 Example 1 to afford the title acid in 86% yield. HRMS calc for $[C_{40}H_{34}ClF_3N_2O_5S+H]$ 747.1902 found 747.1904.

EXAMPLE 13

4-(2-{1-Benzhydryl-5-chloro-2-(2-({[(4-(trifluoromethyl)-benzyl] sulfonyl}-amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step6, Example 1) and [[4-(trifluoromethyl)phenyl] methyl]sulfonyl chloride according to the procedure in Example 1 Step 7 in 77% yield.

Step 2: The ester intermediate was hydrolyzed according to Step 8 Example 1 to afford the title acid in 83% yield. HRMS calc for $[C_{40}H_{34}ClF_3N_2O_5S+H]$ 747.1902 found 747.1901.

EXAMPLE 14

4-{2-[1-Benzhydryl-5-chloro-2-(2-{[(4-fluorobenzyl)-sulfonyl] amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step6, Example 1) and [(4-fluorophenyl)methyl] sulfonyl chloride according to the procedure in Example 1 Step 7 Step 1 in 86% yield.

Step 2: The ester intermediate was hydrolyzed according to Step 8 Example 1 to afford the title acid in 94% yield. HRMS calc for $[C_{39}H_{34}ClFN_2O_5S+H]$ 697.1934 found 697.1938.

EXAMPLE 15

4-{2-[1-Benzhydryl-5-chloro-2-(2-{[(4-chlorobenzyl)sulfonyl] amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step6, Example 1) and [(4-chlorophenyl-)methyl] sulfonyl chloride according to the procedure in Example 1 Step 7 in 73% yield.

Step 2: The ester intermediate was hydrolyzed according to Step 8 Example 1 to afford the title acid in 99% yield. HRMS calc for $[C_{39}H_{34}Cl_2N_2O_5S+H]$ 713.1638 found 713.1643.

EXAMPLE 16

2-(2-{[(2-Aminobenzyl)sulfonyl]amino}ethyl)-4-{2-[1-benzhydryl-5-chloro-1H-indol-3-yl]ethoxy}benzoic acid Step 1: To methyl 4-{2-[1-benzhydryl-5-chloro-2-{2-[2-nitrobenzyl] benzyl}-sulfonyl)amino]ethyl}-1H-indol-3-yl)ethoxy]benzoate, Example 9, step 1, (1.0 equiv) in $CH_2Cl_2$ (0.014 M) was added a mixture of tin(II) chloride dihydrate (3.0 equiv) dissolved in concentrated HCl. After 16 h the mixture was basified (pH 10) with 3 N NaOH and extracted with $CH_2Cl_2$. The combined organic phase was washed with brine, dried over sodium sulfate and purified by column chromatography (gradient elution using 20% EtOAc-hexanes→50% EtOAc-hexanes) to afford 83% of the desired product.

Step 2: The ester intermediate was hydrolyzed according to Step 8 Example 1 to afford the title acid in 83% yield. HRMS calc for $[C_{39}H_{36}ClN_3O_5S+H]$ 694.2137 found 694.2136.

EXAMPLE 17

4-{2-[1-Benzhydryl-5-chloro-2-(2-{[(dimethylamino)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step6, Example 1) and dimethylsulfamoyl chloride according to the procedure in Example 1 Step 7 in 49% yield.

Step 2: The ester intermediate was hydrolyzed according to Step 8 Example 1 to afford the title acid in 95% yield. HRMS calc for $[C_{34}H_{34}ClN_3O_5S+H]$ 632.1981 found 632.1984.

EXAMPLE 18

4-{2-[1-Benzhydryl-5-chloro-2-(2-{[(3,4-difluorobenzyl)sulfonyl] amino}-ethyl)-1H-indol-3-yl]ethoxy}benzoic acid Step 1: To 3,4-difluorobenzyl bromide (1.0 equiv) in $H_2O$ (0.74 M) was added sodium sulfite (1.1 equiv). The mixture was heated to reflux for 16 hours then cooled to room temperature. The white precipitate was filtered and dried to afford 95% of the sodium sulfonate intermediate.

Step 2: To 3,4-difluorobenzyl sodium sulfonate (7.6 equiv) in $CH_2Cl_2$ (0.76 M) was added DMF (5.6 equiv) and $SOCl_2$ (30 equiv). After 1 h the mixture was concentrated and azeotroped with toluene. The residue was suspended in $CH_2Cl_2$ (0.38 M) and methyl 4-{2-[2-(2-aminoethyl)-1-benzhydryl-5-chloro-1H-indol-3-yl] ethoxy}benzoate (Step6, Example 1) (1.0 equiv) and sat. $NaHCO_3$ (0.76 M) were added. After 1 h the mixture was poured into $H_2O$ and extracted with $CH_2Cl_2$. The combined organic phase was washed with brine, dried over sodium sulfate and purified by column chromatography (gradient elution using 20% EtOAc-hexanes→40% EtOAc-hexanes) to afford 94% of the methyl ester intermediate.

Step 3: The methyl ester was hydrolyzed according to Step 8 Example 1 to afford the title acid in 93% yield. HRMS calc for $[C_{39}H_{33}ClF_2N_2O_5S+H]$ 715.184 found 715.1843.

EXAMPLE 19

4-{2-[1-benzhydryl-5-chloro-2-(2-{[(2-naphthylmethyl)sulfonyl] amino}ethyl)-1H-indol-3-yl]ethoxy}benzoic acid Step 1: The sulfonyl chloride intermediate was prepared from 2-(bromomethyl)naphthalene according to the procedure in Example 18 Step 1–2 in 34% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 58% yield.

Step 2: The ester intermediate was hydrolyzed according to Step 8 Example 1 to afford the title acid in 74% yield. HRMS calc for $[C_{43}H_{37}ClN_2O_5S+H]$ 729.2185 found 729.2189.

EXAMPLE 20

3-({[(2-{1-benzhydryl-3-[2-(4-carboxyphenoxy) ethyl]-5-chloro-1H-indol-2-yl}ethyl)amino] sulfonyl}methyl)benzoic acid Step 1: The sulfonyl chloride intermediate was prepared from methyl 3-(bromomethyl)benzoate according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 23% yield.

Step 2: The ester intermediate was hydrolyzed according to Step 8 Example 1 to afford the title diacid in 93% yield. HRMS calc for $[C_{40}H_{35}ClN_2O_7S+H]$ 723.1926 found 723.1932

EXAMPLE 21

4-(2-{1-benzhydryl-5-chloro-2-[2-({[(E)-2-phenylethenyl] sulfonyl}amino)ethyl'1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step6, Example 1) was added trans-α-styrenesulfonyl chloride according to the procedure in Example 1 Step 7 to generate the product in 66% yield.

Step2—The ester intermediate was hydrolyzed according to Step 8 Example 1 to afford the title acid in 98% yield. HRMS calc for $[C_{40}H_{35}ClN_2O_5S+H]$ 691.2028 found 691.2034.

EXAMPLE 22

4-{2-[1-benzhydryl-5-chloro-2-(2-{[(trifluoromethyl)sulfonyl]amino}ethyl)-1H-indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1) was added trifluoromethylsulfonyl chloride according to the procedure in Example 1 Step 7 to generate the product in 49% yield.

Step2—The ester intermediate was hydrolyzed according to Step 8 Example 1 to afford the title acid in 100% yield. HRMS calc for $[C_{33}H_{28}ClF_3N_2O_5S+H]$ 657.1432 found 657.1435.

EXAMPLE 23

4-[2-(1-benzhydryl-5-chloro-2-{2-[ (cyclopropylsulfonyl)amino]ethyl}-1H-indol-3-yl)ethoxy]benzoic acid Step 1: To the methyl 4-{2-[2-(2-aminoethyl)-1-benzhydryl-5-chloro-1H-indol-3-yl]ethoxy}benzoate (Step6, Example 1) was added cyclopropanesulfonyl chloride according to the procedure in Example 1 Step 7 to generate the product in 75% yield.

Step2—The ester intermediate was hydrolyzed according to Step 8 Example 1 to afford the title acid in 84% yield. HRMS calc for $[C_{35}H_{33}ClN_2O_5S+H]$ 629.1872 found 629.1874.

EXAMPLE 24

4-(2-{1-benzhydryl-2-[2-({[3,5-bis(trifluoromethyl)benzyl] sulfonyl}amino)ethyl]-5-chloro-1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step6, Example 1) was added 3,5-bis(trifluoromethyl)benzylsulfonyl according to the procedure in Example 1 Step 7 to generate the product in 79% yield.

Step2—The ester intermediate was hydrolyzed according to Step 8 Example 1 to afford the title acid in 81% yield. HRMS calc for $[C_{41}H_{33}ClF_6N_2O_5S+H]$ 815.1776 found 815.1776.

EXAMPLE 25

2-{[(2-{1-benzhydryl-3-[2-(4-carboxyphenoxy) ethyl]-5-chloro-1H-indol-2-yl}ethyl)amino] sulfonyl}benzoic acid Step 1: To the methyl 4-{2-[2-(2-aminoethyl)-1-benzhydryl-5-chloro-1H-indol-3-yl]ethoxy}benzoate (Step6, Example 1) was added methyl (2-chlorosulfonyl)benzoate according to the procedure in Example 1 Step 7 to generate the product in 100% yield.

Step2—The ester intermediate was hydrolyzed according to Step 8 Example 1 to afford the title acid in 61% yield. HRMS calc for $[C_{39}H_{33}ClN_2O_7S+H]$ 709.177 found 709.1772.

EXAMPLE 26

4-[2-(1-benzhydryl-5-chloro-2-{2-[(2-naphthylsulfonyl)amino] ethyl}-1H-indol-3-yl)ethoxy]benzoic acid Step 1: To the methyl 4-{2-[2-(2-aminoethyl)-1-benzhydryl-5-chloro-1H-indol-3-yl]ethoxy}benzoate (Step6, Example 1) was added 2-naphthalenesulfonyl chloride according to the procedure in Example 1 Step 7 to generate the product in 53% yield.

Step2—The ester intermediate was hydrolyzed according to Step 8 Example 1 to afford the title acid in 100% yield. HRMS calc for $[C_{42}H_{35}ClN_2O_5S+H]$ 715.2028 found 715.2034.

EXAMPLE 27

4-{2-[1-benzhydryl-5-chloro-2-(2-{[(3,5-dichlorophenyl)sulfonyl] amino}ethyl)-1H-indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1) was added 3,5-dichlorobenzenesulfonyl chloride according to the procedure in Example 1 Step 7 to generate the product in 60% yield.

Step2—The ester intermediate was hydrolyzed according to Step 8 Example 1 to afford the title acid in 88% yield. HRMS calc for $[C_{38}H_{31}Cl_3N_2O_5S+H]$ 733.1092 found 733.1096.

EXAMPLE 28

4-{2-[1-benzhydryl-5-chloro-2-(2-{[(3,4-dichlorophenyl)sulfonyl] amino}ethyl)-1H-indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1) was added 3,4-dichlorobenzenesulfonyl chloride according to the procedure in Example 1 Step 7 to generate the product in 60% yield.

Step2—The ester intermediate was hydrolyzed according to Step 8 Example 1 to afford the title acid in 80% yield. HRMS calc for $[C_{38}H_{31}Cl_3N_2O_5S+H]$ 733.1092 found 733.1094.

EXAMPLE 29

4-{2-[1-benzhydryl-5-chloro-2-(2-{[(2,3-dichlorobenzyl)sulfonyl] amino}ethyl)-1H indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1) was added (2,3-dichlorophenyl)-methyl] sulfonyl chloride according to the procedure in Example 1 Step 7 to generate the product in 50% yield.

Step2—The resulting ester was hydrolyzed by stirring with KOH (67 mg, 5 equiv.) in THF (5 mL) MeOH (5 mL) and $H_2O$ (2 mL). The reaction was monitored by TLC (10% MeOH—$CH_2Cl_2$) for the disappearance of starting material. The mixture was stirred overnight at room temperature and then concentrated, diluted with $H_2O$, and acidified to pH 2–4 using 1 M HCl. The aqueous phase was extracted with EtOAc and the organic phase was washed with brine, dried over sodium sulfate, and concentrated to afford the desired product in 98% yield. HRMS calc for $[C_{39}H_{33}Cl_3N_2O_5S+H]$ 747.1249 found 747.1254.

EXAMPLE 30

4-{2-[1-benzhydryl-5-chloro-2-(2-{[(2,4-dichlorobenzyl)sulfonyl] amino}ethyl)-1H-indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1) was added (2,4-dichlorophenyl)-methyl] sulfonyl chloride according to the procedure in Example 1 Step 7 to generate the product in 98% yield.

Step2—The ester intermediate was hydrolyzed according to Step 2 Example 29 to afford the title acid in 90% yield. HRMS calc for $[C_{39}H_{33}Cl_3N_2O_5S+H]$ 747.1249 found 747.1255.

EXAMPLE 31

4-{2-[1-benzhydryl-5-chloro-2-(2-{[(2,4-dichlorobenzyl)sulfonyl] amino}ethyl)-1H indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1) was added (2-chlorophenyl)-methyl]sulfonyl chloride according to the procedure in Example 1 Step 7 to generate the product in 86% yield.

Step2—The ester intermediate was hydrolyzed according to Step 2 Example 29 to afford the title acid in 90% yield. HRMS calc for $[C_{39}H_{34}Cl_2N_2O_5S+H]$ 713.1638 found 713.1644.

EXAMPLE 32

4-{2-[1-benzhydryl-5-chloro-2-(2-{[(4-chloro-2-nitrobenzyl)sulfonyl] amino}ethyl)-1H-indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1)was added [(4-chloro-2-nitro)-methyl] sulfonyl chloride according to the procedure in Example 1 Step 7 to generate the product in 74% yield.

Step2—The ester intermediate was hydrolyzed according to Step 2 Example 29 to afford the title acid in 90% yield. HRMS calc for $[C_{39}H_{33}Cl_2N_3O_7S+H]$ 758.1489 found 758.1494.

Method I

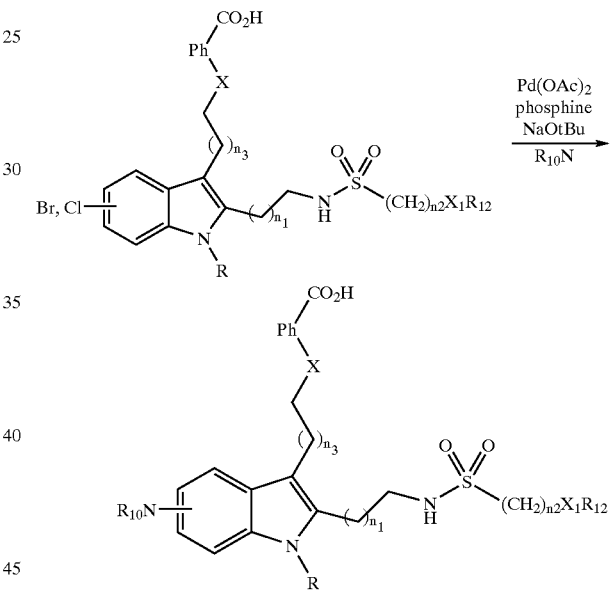

The acid resulting from Method A, or any subsequent method could be used as a subtrate for palladium catalyzed amination reaction using a base, an amine, a phosphine ligand and palladium reagent.

EXAMPLE 33

4-[2-(1-benzhydryl-2-{2-[(benzylsulfonyl)amino] ethyl}-5-morpholin-4-yl-1H-indol-'3-yl)ethoxy]benzoic acid Step 1—A flask was charged with tris(dibenzylideneacetone) dipalladium(0) (0.01 eq.), 2-(di-t-butylphosphino) biphenyl (0.04 eq.), sodium t-butoxide (2.4 eq.) and the acid from step 8 (1.0 eq.). 1.5 ml toluene (1.0 M) was added to the flask followed by morpholine (1.2 eq.) The reaction was heated to reflux for five hours. The reaction mixture was partitioned between 5% hydrochloric acid and dietheyl ether. The organic layer was washed with distilled water, followed by brine, dried over sodium sulfate and concentrated. The product was purified by preparatory LC-MS to afford 7.8% of the desired product. HRMS calc for [$C_{43}H_{43}N_3O_6S$+H] 730.2945 found 730.2945.

EXAMPLE 34

4-{2-[1-Benzhydryl-5-chloro-2-(2-{[(2-cyanobenzyl)-sulfonyl] amino}ethyl)-1H-indol-3-yl] ethoxy}benzoic acid Step 1: (2-Cyano-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (2-cyano-phenyl)-methanesulfonyl chloride according to Example 1 Step 7 as a white solid in 72% yield.

Step3—The ester intermediate was hydrolyzed according to Step 8 Example to afford the title acid in 74% yield. MS (ES) m/z (M−1) 702.0; HRMS Calcd. for $C_{40}H_{35}ClN_3O_5S$ (M+1): 704.1980. Found: 704.1984. Anal. Calcd. for $C_{40}H_{34}ClN_3O_5S$: C, 68.22; H, 4.87; N, 5.97. Found: C, 67.92; H, 5.11; N, 5.54.

EXAMPLE 35

4-{2-[1-benzhydryl-5-chloro-2-(2-{[(3,5-difluorobenzyl)-sulfonyl] amino}ethyl)-1H-indol-3-yl] ethoxy}benzoic acid Step 1: The sulfonyl chloride intermediate was prepared from 3,5-difluorobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy)benzoate (Step 6, Example 1) according to the procedure in Example 1 Step 7 in 78% yield.

Step 2: The ester intermediate was hydrolyzed according to Step 8 Example 1 to afford the title diacid in 83% yield. HRMS calc for [$C_{39}H_{33}ClF_2N_2O_5S$+H] 715.184 found 715.1842.

EXAMPLE 36

4-{2-[1-Benzhydryl-5-chloro-2-(2-{[(3-cyanobenzyl)-sulfonyl] amino}ethyl)-1H-indol-3-yl] ethoxy}benzoic acid Step 1: (3-Cyano-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (3-cyano-phenyl)-methanesulfonyl chloride according to Example 1 Step 7.

Step 3: The ester intermediate was hydrolyzed according to Step 8 Example 1 to afford the title acid in 81% yield. MS (ES) m/z (M−1) 702.1; HRMS Calcd. for $C_{40}H_{33}ClN_3O_5S$ (M−1):702.1834. Found: 702.1833. Anal. Calcd. for $C_{40}H_{34}ClN_3O_5S$·0.8$H_2O$: C, 67.00; H, 5.00; N, 5.86. Found: C, 67.22; H, 5.19; N, 5.44.

EXAMPLE 37

4-{2-[1-Benzhydryl-5-chloro-2-(2-{[(4-cyanobenzyl)-sulfonyl] amino}ethyl)-1H-indol-3-yl] ethoxy}benzoic acid Step 1: (4-Cyano-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1)and (4-cyano-phenyl)-methanesulfonyl chloride according to Example 1 Step 7.

Step 3: The ester intermediate was hydrolyzed according to Step 8 Example 1 to afford the title acid in 77% yield.MS (ES) m/z (M−1) 702.1; HRMS Calcd. for $C_{40}H_{35}ClN_3O_5S$ (M+1): 704.1980. Found: 704.1981. Anal. Calcd. for $C_{40}H_{34}ClN_3O_5S$: C, 68.22; H, 4.87; N, 5.97. Found: C, 68.09; H, 4.97; N, 5.73.

EXAMPLE 38

4-(2-{1-Benzhydryl-5-chloro-2-[2-({[4-(1piperidinyl-sulfonyl)benzyl] sulfonyl}amino)ethyl]-1H-indol-3-yl}ethoxy)benzoic acid Step 1:[4-(Piperidine-1-sulfonyl)-phenyl]-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and 4-(Piperidine-1-sulfonyl)-phenyl]-methanesulfonyl according to Example 1 Step 7.

Step3—The ester intermediate was hydrolyzed according to Step 8 Example 1 to afford the title acid in 73% yield. MS (ES) m/z (M−1) 824.2; HRMS Calcd. for $C_{44}H_{43}ClN_3O_7S_2$ (M−1):824.2236. Found: 824.2246. Anal. Calcd. for $C_{44}H_{44}ClN_3O_7S_2$·0.5$H_2O$: C, 63.25; H, 5.43; N, 5.03. Found: C, 62.85; H, 5.64; N, 4.64.

EXAMPLE 39

4-(2-{2-[2-({[4-Aminosulfonyl)benzyl]sulfonyl}-amino)ethyl]-1-benzhydryl-5-chloro-1H-indol-3-yl}ethoxy)benzoic acid Step 1: (4-Sulfamoyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (4-Sulfamoyl-phenyl)-methanesulfonyl chloride according to Example 1 Step 7.

Step3—The ester intermediate was hydrolyzed according to Step 8 Example 1 to afford the title acid in 69% yield. MS (ES) m/z (M−1) 755.9; HRMS Calcd. for $C_{39}H_{35}ClN_3O_7S_2$ (M−1): 756.1613. Found: 756.1612. Anal. Calcd. for $C_{39}H_{36}ClN_3O_7S_2$: C, 61.77; H, 4.79; N, 5.54. Found: C, 61.93; H, 5.12; N, 5.19.

EXAMPLE 40

4-(2-{1-Benzhydryl-5-chloro-2-[2-(4-methanesulfo-nyl-phenylmethanesulfonylamino)-ethyl]-1H-indol-3-yl}-ethoxy)-benzoic acid Step 1: ((4-Methanesulfonyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) ((4-Methanesulfonyl-phenyl)-methanesulfonyl chloride according to Example 1 Step 7.

Step3: The ester intermediate was hydrolyzed according to Step 8 Example 1 to afford the title acid in 75% yield. MS (ES) m/z (M−1) 755.0; HRMS Calcd. for $C_{40}H_{38}ClN_2O_7S_2$ (M+1): 757.1804. Found: 757.1804. Anal. Calcd. for $C_{40}H_{37}ClN_2O_7S_2 \cdot H_2O$: C, 61.96; H, 5.07; N, 3.61. Found: C, 61.82; H, 5.10; N, 3.48.

EXAMPLE 41

4-(2-{1-Benzhydryl-5-chloro-2-[2-(4-diethylsulfa-moyl-phenylmethanesulfonylamino)-ethyl]-1H-in-dol-3-yl}-ethoxy)-benzoic acid Step 1: (4-Diethylsulfamoyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (4-Diethylsulfamoyl-phenyl)-methanesulfonyl chloride according to Example 1 Step 7.

Step 3: The ester intermediate was hydrolyzed according to Step 8 Example 1 to afford the title acid in 66% yield. MS (ES) m/z (M−1) 812.1; HRMS Calcd. for $C_{43}H_{45}ClN_3O_7S_2$ (M+1): 814.2382. Found: 814.2385. Anal. Calcd. for $C_{43}H_{44}ClN_3O_7S_2 \cdot 0.3H_2O$: C, 62.99; H, 5.48; N, 5.14. Found: C, 62.91; H, 5.67; N, 4.79.

EXAMPLE 42

4-{3-[1-Benzhydryl-5-chloro-2-(2-phenylmethane-sulfonylamino-ethyl)-1H-indol-3-yl]-propyl}-ben-zoic acid Step 1: A mixture of methyl4-iodobenzoate (5.3 g, 20.2 mmol), allyl alcohol (1.78 g, 30.3 mmol), $NaHCO_3$ (4.24 g, 50.5 mmol), $Pd(OAc)_2$ (0.14 g, 0.60 mmol), (n-Bu)$_4$NBr (6.55 g, 20.2 mmol) and 4-A molecular Sieves (4.1 g) in anhydrous DMF (69 mL) was stirred at room temperature for 4 days. The reaction mixture was filtered through celite and the filtrate poured onto water and extracted with EtOAc. Organic layer was washed with brine, dried ($Na_2SO_4$), and concentrated under vaccum. Flash chromatography (silica gel, 10–20% EtOAc-hexanes) gave 2.11 g (85% based on the recovered starting material) of the desired 4-(3-Oxo-propyl)-benzoic acid methyl ester as a clear oil.

Step 2: To a solution of 5-chloro-2-methylindole (0.86 g, 5.2 mmol) and 4-(3-Oxo-propyl)-benzoic acid methyl ester (1.0 g, 5.2 mmol) in methylene chloride (50 mL), was added TFA (1.78 g, 15.6 mmol), followed by triethylsilane (1.81 g, 15.6 mmol). The reaction mixture was stirred overnight, quenched with sat. $NaHCO_3$ solution (50 mL), and the organic layer was washed with sat. $NaHCO_3$ solution, water, brine, and dried ($Na_2SO_4$). Solvent was removed under reduced pressure, and the residue was purified by flash column chromatography with 10–20% EtOAc/hexanes to yield the desired product in 94% (1.67 g) yield.

Step 3: To a solution of the product from step 2 (1.66 g, 4.86 mmol) in DMF (20 mL) was added NaH (60% in mineral oil, 0.24 g, 5.83 mmol) under $N_2$ atmosphere. The mixture was stirred for 1 h at room temperature, followed by the dropwise addition of benzhydryl bromide (1.8 g, 7.29 mmol) in DMF (5 mL). This reaction mixture was stirred overnight at room temperature. Water (500 mL) was added to reaction mixture, it was extracted with EtOAc, washed with brine, dried ($Na_2SO_4$), and concentrated under reduced pressure to a brown syrup, which was purified by silicagel chromatography using 10% EtOAc/hexanes as eluent to isolate 4 as a white solid in 59% (1.47 g) yield.

Step 4: The product from above (1.46 g, 2.87 mmol) was dissolved in $CCl_4$ (14.5 mL), followed by the addition of NBS (1.02 g, 5.73 mmol) and benzoyl peroxide (2 mg). The reaction mixture was heated to reflux for 1 h (until all the starting material disappeared). This mixture was cooled to room temperature, filtered and the solid was washed with $CCl_4$. The filtrate was evaporated to a brown residue, which was dissolved in acetone (40 mL) and water (4 mL), $Ag_2CO_3$ (1.75 g, 3.16 mmol) was then added to this solution and after being stirred overnight at room temperature, it was filtered through celite, the solvent was evaporated under reduced pressure, and water was added to the residue. It was extracted with EtOAc, washed with brine, dried ($Na_2SO_4$), and evaporated to a syrup, which was purified by 10% EtOAc/hexanes to isolate the 2-formyl indole (1.13 g) in 75% yield. Alternatively the dibromide from the reaction with NBS could be poured into DMSO (10–20% concentration by weight) and stirred for 30 minutes at room temperature. When the reaction was deemed complete it was poured into water and the resulting precipitate was isolated by filtration, the cake was washed with water and dried to yield an essentially quantitative yield.

Step 5: To a solution of the 2 formyl indole from above (0.52 g, 1 mmol) in $CH_3NO_2$ (6.2 mL) was added $NH_4OAC$ (0.077 g, 1 mmol), the mixture was heated to reflux for 1 h, $NH_4OAc$ (0.077 g, 1 mmol) was then added, heating at reflux was continued for an additional 1 h, $NH_4Oac$ (0.077 g, 1 mmol) was added again and the heating continued for further 1 h. The reaction mixture was allowed to attain room temperature, EtOAc (50 mL) was added, followed by the addition of 100 mL water. The aqueous layer was extracted with EtOAc, and the combined organic layers were washed with brine, dried ($Na_2SO_4$), and evaporated to a yellow foam, which was subjected to chromatographic purification using 10% EtOAc/hexanes as an eluent to yield 6 as a yellow foam in 68% yield (0.38 g).

Step 6: Zn(Hg) was made by adding $HgCl_2$ (3.4 g, 7.2 mmol) to a mixture of Zn-dust (34.68 g, 530.35 mmol) and 5% HCl (38 mL) in a 100 mL beaker, this mixture was stirred vigorously for 10 min. Aqueous phase was decanted and added 38 mL of 5% HCl again and the mixture was stirred for 10 min. Aqueous phase was decanted. This solid was added to the vinyl nitro compound 6 (15 g, 26.57 mmol) in THF (660 mL) and conc. HCl (64.5 mL). This mixture was stirred at room temperature for 1 h, then at reflux for 15 min. The reaction mixture was cooled to room temperature and filtered through celite. Aq. $NH_4OH$ solution (200 mL) was added to the filtrate, stirred for 15 min and THF was removed under reduced pressure. The aqueous layer was extracted with $CH_2Cl_2$, combined organic layer was washed with brine, dried (Na2SO4) and concentrated to a brown foam, which was purified by column chromatography by eluting the column with $CHCl_3$ in the beginning to remove nonpolar impurities then with 2% $MeOH/CHCl_3$ to isolate the desired amine in 46% yield (6.1 g)

Step 7: To the amine(1.0 equiv.) and sat. $NaHCO_3$ (0.14 M) in $CH_2Cl_2$ (0.07 M) was added α-toluenesulfonyl chloride (1.0 equiv.). After 1 h the mixture was poured into saturated sodium bicarbonate and extracted with $CH_2Cl_2$. The combined organic phase was washed with brine, dried over sodium sulfate and purified by column chromatography to afford 84% of the desired product.

Step 8: The resulting ester was hydrolyzed by stirring with 1N NaOH (5 equiv.) in THF (0.07 M) and enough MeOH to produce a clear solution. The reaction was monitored by TLC (10% $MeOH$—$CH_2Cl_2$) for the disappearance of starting material. The mixture was stirred overnight at room temperature and then concentrated, diluted with $H_2O$, and acidified to pH 2–4 using 1 M HCl. The aqueous phase was extracted with EtOAc and the organic phase was washed with brine, dried over sodium sulfate, and concentrated to afford the desired product in 100% yield. HRMS calc for $[C_{40}H_{37}ClN_2O_4S+H]$ 677.2235 found 677.224.

EXAMPLE 43

4-{3-[1-benzhydryl-5-chloro-2-(2-{[(3,5-dichlorobenzyl)sulfonyl] amino}ethyl)-1H-indol-3-yl] propyl}benzoic acid Step 1: This compound was prepared from the intermediate in Example 42 step 6 and (3,5-dichlorophenyl)-methyl] sulfonyl chloride according to the procedure in Example 43 Step 7 which yielded 98% of the desired product.

Step 2: The ester intermediate was hydrolyzed according to Step 8 Example 42 to afford the title acid in 100% yield. HRMS calc for $[C_{40}H_{35}Cl_3N_2O_4S+H]$ 745.1456 found 745.1458.

EXAMPLE 44

4-{3-[1-benzhydryl-5-chloro-2-(2-{[(3,4-dichlorobenzyl)sulfonyl] amino}ethyl)-1H-indol-3-yl] propyl}benzoic acid Step 1: This compound was prepared from the intermediate in Example 42 step 6 and (3,4-dichlorophenyl)-methyl] sulfonyl chloride according to the procedure in Example 43 Step 7 which yielded 96% of the desired product.

Step 2: The ester intermediate was hydrolyzed according to Step 8 Example 42 to afford the title acid in 98% yield. HRMS calc for $[C_{40}H_{35}Cl_3N_2O_4S+H]$ 745.1456 found 745.1458.

EXAMPLE 45

4-[2-(1-benzhydryl-5-chloro-2-(2-[ (methylsulfonyl) amino]ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step6, Example 1)was added methanesulfonyl chloride according to the procedure in Example 4 Step 1 to generate the product in 92% yield.

Step 2: The ester intermediate was hydrolyzed according to Step 8 Example 1 to afford the title acid in 100% yield. HRMS calc for $[C_{33}H_{31}ClN_2O_5S+H]$ 603.1715 found 603.1717.

EXAMPLE 46

4-[2-(1-benzhydryl-5-chloro-2-{2-[ (phenylsulfonyl) amino]ethyl}-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step6, Example 1)was added benzenesulfonyl chloride according to the procedure in Example 4 Step 1 to generate the product in 90% yield.

Step 2: The ester intermediate was hydrolyzed according to Step 8 Example 1 to afford the title acid in 90% yield. HRMS caic for $[C_{38}H_{33}ClN_2O_5S+H]$ 665.1872 found 665.1869

EXAMPLE 47

4-(2-{1-benzhydryl-5-chloro-2-[2-({[3-(trifluoromethyl)benzyl] sulfonyl}amino)ethyl]-1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step6, Example 1)was added {[3-(trifluoromethyl)phenyl] methyl}sulfonyl chloride according to the procedure in Example 1 Step 7 to generate the product in 74% yield.

Step 2: The ester intermediate was hydrolyzed according to Step 8 Example 1 to afford the title acid in 86% yield. HRMS calc for $[C_{40}H_{34}ClF_3N_2O_5S+H]$ 747.190 found 747.1904

EXAMPLE 48

2-{[(2-{[(2-{1-benzhydryl-3-[2-(4-carboxyphenoxy) ethyl]-5-chloro-1H-indol-2-yl}ethyl)amino] sulfonyl}ethyl)amino]carbonyl}benzoic acid Step 1: To the methyl 4-{2-[2-(2-aminoethyl)-1-benzhydryl-5-chloro-1H-indol-3-yl]ethoxy}benzoate (Step6, Example 1)was added 2-phthalimidoethanesulfonyl chloride according to the procedure in Example 1 Step 7 to generate the product in 78% yield.

Step 2: The ester intermediate was hydrolyzed according to Step 8 Example 1 to afford the title acid in 99% yield. HRMS calc for $[C_{42}H_{38}ClN_3O_8S+H]$ 780.2141 found 780.2148

EXAMPLE 49

4-{2-[{1-benzhydryl-5-chloro-2-(2-{[(3-(pyridinylmethyl)sulfonyl] amino}ethyl)-1H-indol-3-yl] ethoxy}benzoic acid Step 1: To the methyl 4-{2-[2-(2-aminoethyl)-1-benzhydryl-5-chloro-1H-indol-3-yl]ethoxy}benzoate (Step6, Example 1)was added (3-pyridylmethyl)sulfonyl chloride according to the procedure in Example 1 Step 7 to generate the product in 52% yield.

Step 2: The ester intermediate was hydrolyzed according to Step 8 Example 1 to afford the title acid in 94% yield. HRMS calc for $[C_{38}H_{34}ClN_3O_5S-H]$ 678.18349 found 678.18277.

EXAMPLE 50

4-{2-[{1-benzhydryl-5-chloro-2-(2-{[(4-(pyridinyl-methyl)sulfonyl] amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step6, Example 1)was added (4-pyridylmethyl)sulfonyl chloride according to the procedure in Example 1 Step 7 to generate the product in 57% yield.

Step 2: The ester intermediate was hydrolyzed according to Step 8 Example 1 to afford the title acid in 100% yield. m/z (M-1) HRMS calc for [$C_{38}H_{34}ClN_3O_5S$—H] 678.18349 found 678.18249

EXAMPLE 51

4-{2-[{1-benzhydryl-5-chloro-2-(2-{[(2-(pyridinyl-methyl)sulfonyl] amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step6, Example 1)was added (2-pyridylmethyl)sulfonyl chloride according to the procedure in Example 1 Step 7 to generate the product in 42% yield.

Step 2: The ester intermediate was hydrolyzed according to Step 8 Example 1 to afford the title acid in 56% yield. HRMS calc for [$C_{38}H_{34}ClN_3O_5S$—H] 678.18349 found 678.18312

EXAMPLE 52

4-{3-[1-benzhydryl-5-chloro-2-(2-{[(2,6-dimethyl-benzyl)-sulfonyl] amino}ethyl)-1H-indoly-3-yl]propyl}benzoic acid Step 1: The sulfonyl chloride intermediate was prepared from 2,6-dimethylbenzyl chloride according to the procedure in Example 18 Step 1–2 in 100% yield.

Step 2: The methyl ester was prepared from the sulfonyl chloride and the intermediate in Example 42 step 6 according to the procedure in Example 42 Step 7 in 30% yield.

Step 3: The ester intermediate was hydrolyzed according to Step 8 Example 42 to afford the title acid in 100% yield. HRMS calc for [$C_{42}H_{41}ClN_2O_4S$—H] 703.24028 found 703.23973

EXAMPLE 53

4-{2-[1-benzhydryl-5-chloro-2-(2-{[(cyclohexylm-ethyl)-sulfonyl] amino}ethyl)-1H-indol-3-yl]ethoxy}benzoic acid Step 1: The sulfonyl chloride intermediate was prepared from (bromomethyl)cyclohexane according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 20% yield.

Step 3: The ester intermediate was hydrolyzed according to Step 8 Example 1 to afford the title acid in 73% yield. HRMS calc for [$C_{39}H_{41}ClN_2O_5S$—H] 683.23519 found 683.23474

EXAMPLE 54

4-{2-[1-benzhydryl-5-chloro-2-(2-{[(4-nitrobenzyl)sulfonyl] amino}ethyl)-1H-indol-3-yl]ethoxy}benzoic acid Step 1: The sulfonyl chloride intermediate was prepared from 4-nitrobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 80% yield.

Step 3: The ester intermediate was hydrolyzed according to Step 8 Example 1 to afford the title compound in 90% yield. HRMS calc for [$C_{39}H_{34}ClN_3O_7S$+H] 724.1879 found 724.1884.

EXAMPLE 55

4-{2-[1-benzhydryl-5-chloro-2-(2-{[(3-nitrobenzyl)sulfonyl] amino} thyl)-1H-indol-3-yl]ethoxy}benzoic acid Step 1: The sulfonyl chloride intermediate was prepared from 3-nitrobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 85% yield.

Step 3: The ester intermediate was hydrolyzed according to Step 8 Example 1 to afford the title compound in 85% yield. HRMS calc for [$C_{39}H_{34}ClN_3O_7S$+H] 724.1879 found 724.1885.

EXAMPLE 56

4-{2-[1-Benzhydryl-5-chloro-2-{2-[({2-nitroben-zyl}-sulfonyl)amino] ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-nitro-a-toluenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{36}ClN_3O_6S$+H] 722.2086 found 722.2088.

EXAMPLE 57

4-{3-[1-benzhydryl-5-chloro-2-(2-{[(4-fluorobenzyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added and (4-Fluoro-phenyl)-methanesulfonyl chloride according to the procedure in Example 1 Step 7 to generate the product in 77% yield.

Step 2: The ester intermediate was hydrolyzed according to Step 8 Example 1 to afford the title acid in 68% yield. HRMS calc for [$C_{40}H_{36}ClFN_2O_4S$+H] 695.2141 found 695.2145.

EXAMPLE 58

4-(3-{1-benzhydryl-5-chloro-2-[2-({[4-(trifluoromethyl)benzyl] sulfnyl}amino)ethyl]-1H-indol-3-yl}propyl)benzoic acid Step 1: To the methyl 4-{2-[2-(2-aminoethyl)-1-benzhydryl-5-chloro-1H-indol-3-yl]propyl}benzoate (Step 6, Example 42) was added and (4-Trifluoro-methylphenyl)-methanesulfonyl chloride according to the procedure in Example 1 Step 7 to generate the product in 50% yield.

Step 2: The ester intermediate was hydrolyzed according to Step 8 Example 1 to afford the title acid in 100% yield. HRMS calc for [$C_{41}H_{36}ClF_3N_2O_4S$+H] 745.2109 found 745.2114.

EXAMPLE 59

4-(3-{1-benzhydryl-5-chloro-2-[2-({[3-(trifluoromethyl)benzyl] sulfonyl}amino)ethyl]-1H-indol-3-yl}propyl)benzoic acid Step 1: To methyl 4-{2-[2-(2-aminoethyl)-1-benzhydryl-5-chloro-1H-indol-3-yl] propyl}benzoate (Step 6, Example 42) was added and (3-Trifluoromethyl-phenyl)-methanesulfonyl chloride according to the procedure in Example 1 Step 7 to generate the product in 56% yield.

Step 2: The ester intermediate was hydrolyzed according to Step 8 Example 1 to afford the title acid in 82% yield. HRMS calc for [$C_{41}H_{36}ClF_3N_2O_4S$+H] 745.2109 found 745.211.

EXAMPLE 60

4-{3-[1-benzhydryl-5-chloro-2-(2-{[(4-chlorobenzyl)sulfonyl] amino}ethyl)-1H-indol-3-yl] propyl}benzoic acid Step 1: To the methyl methyl 4-{2-[2-(2-aminoethyl)-1-benzhydryl-5-chloro-1H-indol-3-yl]propyl}benzoate (Step 6, Example 42) was added and (4-chlorophenyl)methanesulfonyl chloride according to the procedure in Example 1 Step 7 to generate the product in 74% yield.

Step 2: The ester intermediate was hydrolyzed according to Step 8 Example 1 to afford the title acid in 79% yield. HRMS calc for [$C_{40}H_{36}Cl_2N_2O_4S$+H] 711.1846 found 711.1847.

EXAMPLE 61

4-{3-[1-benzhydryl-5-chloro-2-(2-{[(2-pyridinylmethyl)-sulfonyl] amino}ethyl)-1H-indol-3-yl] propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-2-yl-methanesulfonyl chloride chloride according to the procedure in Example 4 Step 1 to generate the product in 75% yield.

Step 2: The ester intermediate was hydrolyzed according to Step 8 Example 1 to afford the title acid in 96% yield. HRMS calc for [$C_{39}H_{36}ClN_3O_4S$+H] 678.2188 found 678.2187.

EXAMPLE 62

4-{3-[1-benzhydryl-5-chloro-2-(2-{[(3-pyridinylmethyl)sulfonyl] amino}ethyl)-1H-indol-3-yl] propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-3-yl-methanesulfonyl chloride chloride according to the procedure in Example 4 Step 1 to generate the product in 75% yield.

Step 2: The ester intermediate was hydrolyzed according to Step 8 Example 1 to afford the title acid in 88% yield.

EXAMPLE 63

4-{3-[1-benzhydryl-5-chloro-2-(2-{[(4-pyridinylmethyl)sulfonyl] amino}ethyl)-1H-indol-3-yl] propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin4-yl-methanesulfonyl chloride chloride according to the procedure in Example 4 Step 1 to generate the product in 75% yield.

Step 2: The ester intermediate was hydrolyzed according to Step 8 Example 1 to afford the title acid in 77% yield. HRMS calc for [$C_{39}H_{36}ClN_3O_4S$—H] 676.20423 found 676.20405

EXAMPLE 64

4-{3-[1-benzhydryl-5-chloro-2-(2-{[(2-chlorobenzyl)sulfonyl] amino}ethyl)-1H-indol-3-yl] propyl}benzoic acid Step 1: The sulfonyl chloride intermediate was prepared from 3-chlorobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 10% yield. Step 3: The ester intermediate was hydrolyzed according to Step 8 Example 1 to afford the title compound in 100% yield. HRMS calc for [$C_{40}H_{36}Cl_2N_2O_4S$—H] 709.17000 found 709.16961

EXAMPLE 65

4-{3-[1-benzhydryl-5-chloro-2-(2-{[(3-nitrobenzyl)sulfonyl] amino}ethyl)-1H-indol-3-yl] propyl}benzoic acid Step 1: The sulfonyl chloride intermediate was prepared from 3-nitrobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 43% yield.

Step 3: The ester intermediate was hydrolyzed according to Step 8 Example 1 to afford the title compound in 88% yield. HRMS calc for [$C_{40}H_{36}ClN_3O_6S$—H] 720.19405 found 720.19398

EXAMPLE 66

4-{3-[1-benzhydryl-5-chloro-2-(2-{[(3-chlorobenzyl)sulfonyl] amino}ethyl)-1H-indol-3-yl]propyl}benzoic acid Step 1: The sulfonyl chloride intermediate was prepared from 3-chlorobenzyl bromide according to the procedure in Example 18 Step 1–2.
Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 27% yield.
Step 3: The ester intermediate was hydrolyzed according to Step 8 Example 1 to afford the title compound in 93% yield. HRMS calc for $[C_{40}H_{36}Cl_2N_2O_4S-H]$ 709.17000 found 709.16963

EXAMPLE 67

4-{3-[1-benzhydryl-5-chloro-2-(2-{[(2,5-dichlorobenzyl)sulfonyl] amino}ethyl)-1H-indol-3-yl]propyl}benzoic acid Step 1: The sulfonyl chloride intermediate was prepared from 2,5-dichlorobenzyl bromide according to the procedure in Example 18 Step 1–2.
Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 59% yield.
Step 3: The ester intermediate was hydrolyzed according to Step 8 Example 1 to afford the title compound in 100% yield. HRMS calc for $[C_{40}H_{35}Cl_3N_2O_4S-H]$ 743.13103 found 743.13079

EXAMPLE 68

4-{3-[1-benzhydryl-5-chloro-2-(2-{[(3-methoxybenzyl)sulfonyl] amino}ethyl)-1H-indol-3-yl]propyl}benzoic acid Step 1: The sulfonyl chloride intermediate was prepared from 3-methoxybenzyl bromide according to the procedure in Example 18 Step 1–2.
Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 20% yield.
Step 3: The ester intermediate was hydrolyzed according to Step 8 Example 1 to afford the title compound in 100% yield. HRMS calc for $[C_{41}H_{39}ClN_2O_5S-H]$ 705.21954 found 705.21909

EXAMPLE 69

4-{3-[2-(2-{[(2-aminobenzyl)-sulfonyl] amino}ethyl)-1-benzhydryl-5-chloro-1H-indol-3yl]propyl}benzoic acid Step 1: The intermediate from Step 1 Example 56 was treated with $SnCl_2$ according to the procedure in Step 1 Example 16 to yield the amino ester in 99% yield.
Step 2: The ester intermediate was hydrolyzed according to Step 8 Example 1 to afford the title acid in 100% yield. HRMS calc for $[C_{40}H_{38}ClN_3O_4S-H]$ 690.21988 found 690.21941

EXAMPLE 70

4-{3-[1-Benzhydryl-5-chloro-2-(2-{[(2-methylbenzyl)sulfonyl] amino}ethyl)-1H-indol-3-yl]propyl}benzoic acid Step 1: The sulfonyl chloride intermediate was prepared from 2-Methylbenzyl bromide according to the procedure in Example 18 Step 1–2 in quantitative yield.
Step 2: The methyl ester was prepared from the sulfonyl chloride and the intermediate in Example 42 step 6 according to the procedure in Example 42 Step 7 in 50% yield.
Step 3: The ester intermediate was hydrolyzed according to Step 8 Example 42 to afford the title acid in 93% yield. HRMS calc for $[C_{41}H_{39}ClN_2O_4S-H]$ 689.22463 found 689.22421

EXAMPLE 71

4-{2-[1-Benzhydryl-5-chloro-2-(2-{[(4-trifluorometoxybenzyl)sulfonyl] amino}ethyl)-1H-indol-3-yl]ethoxy}benzoic acid Step 1: The sulfonyl chloride intermediate was prepared from 4-Trifluorometoxybenzyl bromide according to the procedure in Example 18 Step 1–2 in quantitative yield.
Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 48% yield.
Step 2: The ester intermediate was hydrolyzed according to Step 8 Example 1 to afford the title acid in 85% yield. HRMS calc for $[C_{40}H_{34}ClF_3N_2O_6S-H]$ 761.17054 found 761.17031

EXAMPLE 72

4-{2-[1-Benzhydryl-5-chloro-2-(2-{[(2-fluoro-6-nitrobenzyl)sulfonyl] amino}ethyl)-1H-indol-3-yl]ethoxy}benzoic acid Step 1: The sulfonyl chloride intermediate was prepared from 2-Fluoro, 6-nitrobenzyl bromide according to the procedure in Example 18 Step 1–2 in quantitative yield.
Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 91% yield.
Step 2: The ester intermediate was hydrolyzed according to Step 8 Example 1 to afford the title acid in 100% yield. m/z (M–1) 740.05

EXAMPLE 73

4-{2-[1-Benzhydryl-5-chloro-2-(2-{[(2-dichlorobenzyl)sulfonyl] amino}ethyl)-1H-indol-3-yl]ethoxy}benzoic acid Step 1: The c chloride intermediate was prepared from 3,5-dichlorobenzyl bromide according to the procedure in Example 18 Step 1–2 in theoretical yield.
Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 100% yield.

Step 2: The ester intermediate was hydrolyzed according to Step 8 Example 1 to afford the title acid in 81% yield. m/z (M−1) 747.2. HRMS calc for [$C_{39}H_{33}Cl_3N_2O_5S$—H] 745.11030 found 745.10954.

EXAMPLE 74

4-{2-[1-Benzhydryl-5-chloro-2-(2-{[(2,6-difluorobenzyl)sulfonyl] amino}ethyl)-1H-indol-3-yl]ethoxy}benzoic acid Step 1: The sulfonyl chloride intermediate was prepared from 2,6-difluorobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 86% yield.

Step 3: The ester intermediate was hydrolyzed according to Step 8 Example 1 to afford the title acid in 71% yield. m/z (M−1)714. HRMS calc for [$C_{39}H_{33}ClF_2N_2O_5S$—H] 713.16940 found 713.16906

EXAMPLE 75

4-(2-{1-benzhydryl-5-chloro-2-[2-{[(6-chloro-3-pyridinyl)methyl] sulfonyl}amino)ethyl]-1H-indol-3-yl}ethoxy)benzoic acid Step 1: (6-chloro-3-pyridinyl)-methanol (1.0 eq.) was taken up in dichloromethane and stirred overnight with carbon tetrabromide (1.5 eq.) and 1,3-bis(diphenylphosphino)propane (0.75 eq.) Ether was added to the solution and filtration followed by concentration of the filtrate afforded (6-chloro-3-bromomethyl) pyridine in 62% yield.

Step 2: The sulfonyl chloride intermediate was prepared from the product of Step 1 according to the procedure in Example 18 steps 1–2.

Step 3: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 78% yield Step 4: The ester intermediate was hydrolyzed according to Step 8 Example 1 to afford the title acid in 89% yield. HRMS calc for [$C_{38}H_{33}Cl_2N_3O_5S$—H] 712.14452 found 712.14420.

EXAMPLE 76

4-(2-{1-benzhydryl-5-chloro-2-[2-({[(5,6-dichloro-2-[ pyridinyl)methyl]sulfonyl}amino)ethyl]-1H-indol-3-yl}ethoxy)benzoic acid Step 1: 5,6-dichloro-3-pyridinemethanol (1.0 eq.) was taken up in dichloromethane and stirred overnight with carbon tetrabromide (1.5 eq.) and 1,3-bis(diphenylphosphino)propane (0.75 eq.) Ether was added to the solution and filtration followed by concentration of the filtrate afforded the 5,6-dichloro-3-bromomethylpyridine in 130% yield.

Step 2: The sulfonyl chloride intermediate was prepared from the product of Step 1 according to the procedure in Example 18 steps 1–2 in 81% yield Step 3: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 79% yield Step 4: The ester intermediate was hydrolyzed according to Step 8 Example 1 to afford the title acid in 109% yield. HRMS calc for [$C_{38}H_{32}Cl_3N_3O_5S$—H] 746.10554 found 746.10549.

EXAMPLE 77

4-{2-[1-Benzhydryl-5-chloro-2-(2-{[(3-methoxybenzyl)sulfonyl] amino}ethyl)-1H-indol-3-yl]ethoxy}benzoic acid Step 1: The sulfonyl chloride intermediate was prepared from 3-methoxybenzyl bromide according to the procedure in Example 18 Step 1–2 in 68% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Step 2: The ester intermediate was hydrolyzed according to Step 8 Example 1 to afford the title diacid in 93% yield. HRMS calc for [$C_{39}H_{33}Cl_3N_2O_5S$+Na] 731.1953 found 731.1947.

EXAMPLE 78

4-{2-[1-Benzhydryl-5-chloro-2-(2-{[(3,5-dimethylbenzyl)sulfonyl] amin }ethyl)-1H-indol-3-yl]ethoxy}benzoic acid Step 1: The sulfonyl chloride intermediate was prepared from 3,5-dimethylbenzyl bromide according to the procedure in Example 18 Step 1–2 in 38% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 38% yield.

Step 2: The ester intermediate was hydrolyzed according to Step 8 Example 1 to afford the title diacid in 88% yield. m/z (M−1)705.0 HRMS calc for [$C_{41}H_{39}ClN_2O_5S$—H] 705.21954 found 705.21916.

EXAMPLE 79

4-{2-[1-Benzhydryl-5-chloro-2-(2-{[(2-methylbenzyl)sulfonyl] amino}ethyl)-1H-indol-3-yl]ethoxy}benzoic acid Step 1: The sulfonyl chloride intermediate was prepared from 2-methylbenzyl bromide according to the procedure in Example 18 Step 1–2 in 35% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 35% yield.

Step 2: The ester intermediate was hydrolyzed according to Step 8 Example 1 to afford the title diacid in 90% yield. m/z (M−1)691.0. HRMS calc for [$C_{40_1}H_{37}ClN_2O_5S$—H] 691.20389 found 691.20350

EXAMPLE 80

4-{2-[1-Benzhydryl-5-chloro-2-(2-{[(2,6-dichlorobenzyl)sulfonyl] amino}ethyl)-1H-indol-3-yl]ethoxy}benzoic acid Step 1: The sulfonyl chloride intermediate was prepared from 2,6-dichlorobenzyl bromide according to the procedure in Example 18 Step 1–2 in 3% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step6, Example 1) according to the procedure in Example 1 Step 7 in 3% yield.

Step 2: The ester intermediate was hydrolyzed according to Step 8 Example 1 to afford the title diacid in 92% yield. m/z (M−1)745.0

Method C

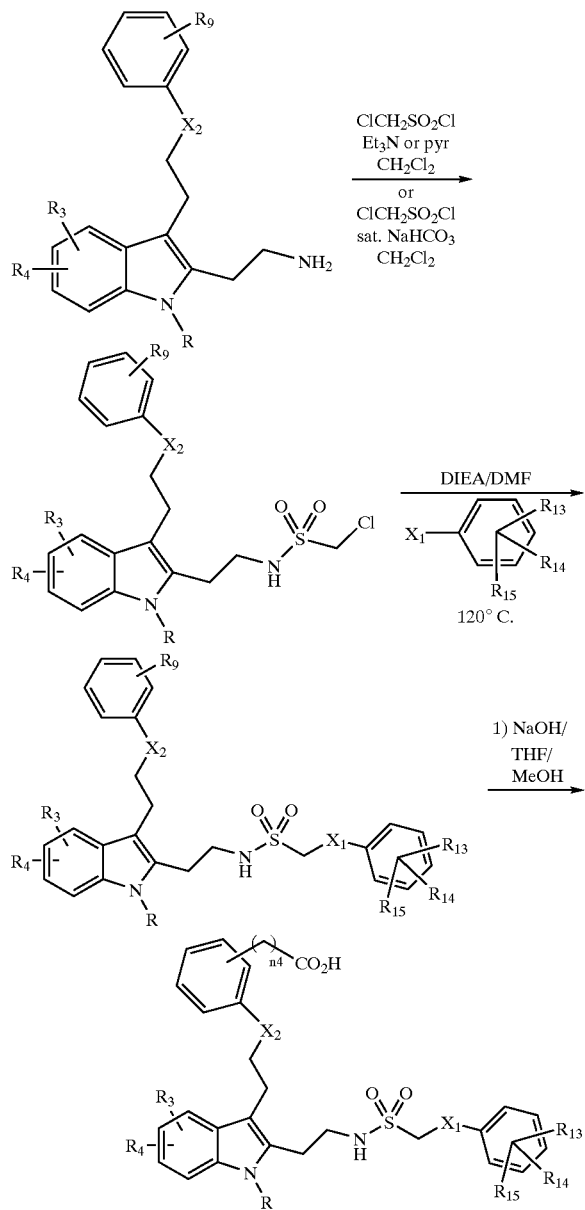

The intermediate amine, synthesized using method A, was treated with chloromethylsulfonyl chloride either under Schott and Baumman conditions or under anhydrous conditions with an organic base yielded a chloromethyl sulfonamide intermediate. This intermediate could be treated with a variety of nucleophiles in DMF with a suitable organic base, Hunigs base, triethylamine etc, and heated until the reaction was complete. The resulting intermediates where then hydrolyzed to yield the final compound. The following examples were synthesized with method C: Examples 81–86.

EXAMPLE 81

4-(2-{1-benzhydryl-5-chloro-[2({[(phenylsulfanyl)-methyl] sulfonyl}amino)ethyl]-1H-indol-3-yl}ethoxy)benzoic acid The title compound was synthesized as depicted in Method C.

Step 1: To the methyl 4-{2-[2-(2-aminoethyl)-1-benzhydryl-5-chloro-1H-indol-3-yl]ethoxy}benzoate (Step6, Example 1) was added chloromethanesulfonyl chloride according to the procedure in Example 1 Step 7 to generate the product in 99% yield.

Step 2: To methyl 4-{2-[1-benzhydryl-5-chloro-2-( 2-{[(chloromethyl)sulfonyl]amino}ethyl)-1H-indol-3-yl]ethoxy}benzoate (0.080M, 1.0 equiv.) and iPr₂NEt (3.4 equiv.) in N,N-dimethylformamide was added thiophenol (2.1–2.5 equiv.) and the mixture was stirred at 120 oC for 3.5 days. The reaction mixture was diluted with EtOAc and washed with water and brine. The combined organic phase was dried over magnesium sulfate and purified by flash chromatography.

Step 3: The ester intermediate was hydrolyzed according to Step 8 Example 1 to afford the title acid in 93% yield. m/z (M−1) 709.11. HRMS calc for [$C_{39}H_{35}ClN_2O_5S_2$—H] 709.16031 found 709.15999.

EXAMPLE 82

4-(2–1-benzhydryl-5-chloro-2-[2-(2,6-dimethyl-phenylsulfanyl methanesulfonylamino)-ethyl]-]-1H-indol-3-yl }-ethoxy)-benzoic acid Step 1: To methyl 4-{2-[1-benzhydryl-5-chloro-2-(2-{[(chloromethyl)sulfonyl]amino}ethyl)-1H-indol-3-yl]ethoxy}benzoate, Example 81 step1, was added 2,6-dimethylthiophenol according to the procedure in Example 81 step 2. The product was purified by the flash chromatography with 25% EtOAc/hexane in 32% yield.

Step2: The ester intermediate was hydrolyzed according to Step 8 Example 42 to afford the title acid in 80% yield. m/z (M−1)751.0. HRMS calc for [$C_{41}H_{39}ClN_2O_5S_2$—H] 737.19161 found 737.19128.

EXAMPLE 83

4-(2-{1-benzhydryl-5-chloro-2-[2-(2-methoxy-phenyl-sulfanylmethanesulfonylamino)-ethyl] ]-1H-indol-3-yl}-ethoxy)-benzoic acid Step 1: To methyl 4-{2-[1-benzhydryl-5-chloro-2-(2-{[(chloromethyl) sulfonyl] amino}ethyl) - '1H - indol- 3- yl]- ethoxy}benzoate, Example 81 step1, was added 2-methoxythiophenol according to the procedure in Example 81 step 2. The product was purified by the flash chromatography 30% EtOAc/hexane in 36% yield.

Step2: The ester intermediate was hydrolyzed according to Step 8 Example 42 to afford the title acid in 94% yield. m/z (M−1) 753.3. HRMS calc for [$C_{40}H_{37}ClN_2O_6S_2$—H] 739.17088 found 739.17052.

EXAMPLE 84

4-(2-{1-benzhydryl-5-chloro-2-[2-(2-chloro-6-methyl-phenylsulfanylmethanesulfonylamino)-ethyl]]-1H-indol-3-yl }-ethoxy)-benzoic acid Step 1: To methyl 4-{2-[1-benzhydryl-5-chloro-2-(2-{[(chloromethyl)sulfonyl] amino}ethyl)-'1H-indol-3-yl]ethoxy}benzoate, Example 81 step1, was added 2-chloro-6-methylthiophenol according to the procedure in Example 81 step 2. The product was purified by the flash chromatography 25% EtOAc/hexane in 46% yield.

Step2: The ester intermediate was hydrolyzed according to Step 8 Example 42 to afford the title acid in 100% yield. m/z (M−1)771.2. HRMS calc for [$C_{40}H_{36}Cl_2N_2O_5S_2$—H] 757.13699 found 757.13730.

EXAMPLE 85

4-(2-{1-benzhydryl-5-chloro-2-[2(3,5-dichloro-phenylsulfanyl methanesulfonylamino)-ethyl]-]-1H-indol-3-yl }-ethoxy)benzoic acid Step1: To methyl 4-{2-[1-benzhydryl-5-chloro-2-(2-{[(chloromethyl)sulfonyl]amino}ethyl)-'1H-indol-3-yl]ethoxy}benzoate, Example 81 step1, was added 3,5-dichlorothiophenol according to the procedure in Example 81 step 2. The product was purified by the flash chromatography 25% EtOAc/hexane in 40% yield.

Step2: The ester intermediate was hydrolyzed according to Step 8 Example 42 to afford the title acid in 98% yield. m/z (M−1)793.2. HRMS calc for [$C_{39}H_{33}Cl_3N_2O_5S_2$—H] 777.08237 found 777.08159.

EXAMPLE 86

4-(2-{1-benzhydryl-5-chloro-2-[2(3,4-dimethoxyphenylsulfanyl methanesulfonylamino)-ethyl-]-1H-indol-3-yl }-ethoxy)benzoic acid Step1: To methyl 4-{2-[1-benzhydryl-5-chloro-2-(2-{[(chloromethyl)-sulfonyl] amino}ethyl)-'1H-indol-3-yl]ethoxy}benzoate, Example 81 step1, was added 3,4-dimethoxythiophenol according to the procedure in Example 81 step 2. The product was purified by the flash chromatography with 35% EtOAc/hexane in 40% yield.

Step2: The ester intermediate was hydrolyzed according to Step 8 Example 42 to afford the title acid compound in 99% yield. m/z (M−1)783.3. HRMS calc for [$C_{41}H_{39}ClN_2O_7S_2$—H] 769.18144 found 769.18120.

Method D

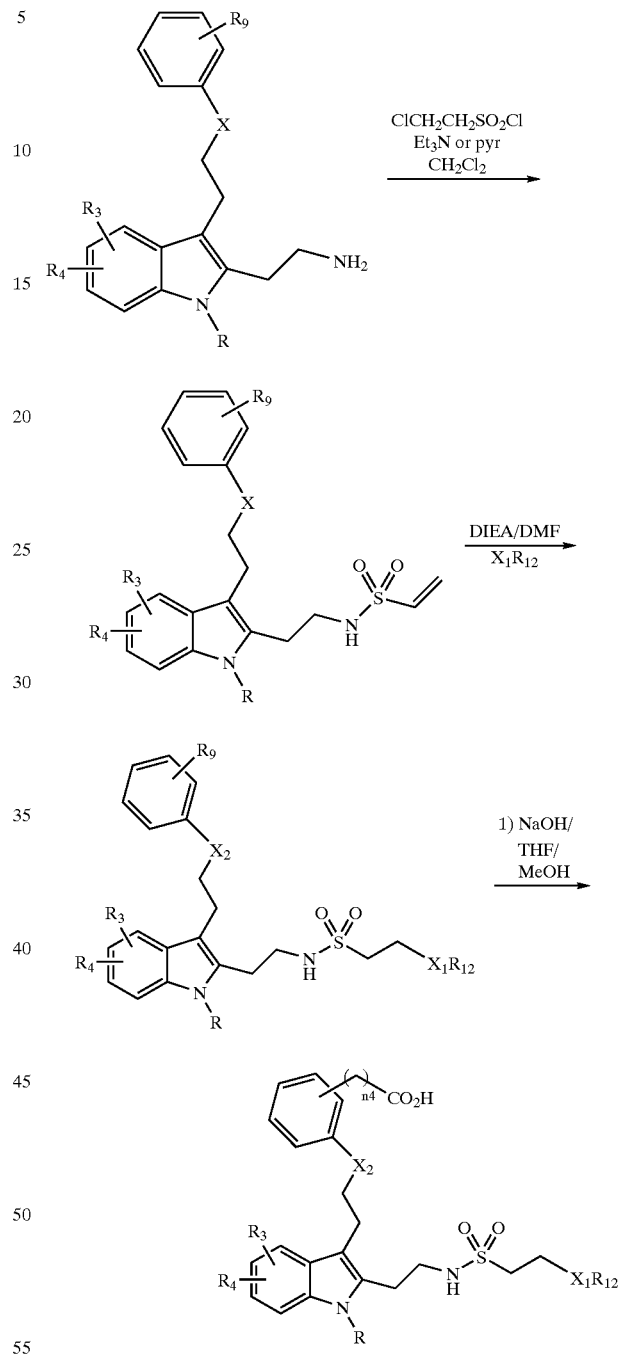

The intermediate amine, synthesized using method A, was treated with chloroethanesulfonyl chloride under anhydrous conditions with an organic base yielded a vinyl sulfonamide intermediate. This intermediate could be treated with a variety of nucleophiles in DMF with a suitable organic base, Hunigs base, triethylamine etc, and heated until the reaction was complete. The resulting intermediates were then hydrolyzed to yield the final compound. The following examples were synthesized with Method D: Examples 87–99 and 100–105, 113–117, and 122–125.

EXAMPLE 87

4-(2-{1-Benzhydryl-5-chloro-2-[2(2-morpholin-4-ylethane sulfonylamino)-ethyl]-1H-ind l-3-yl}-ethoxy)-benzoic acid The title compound was synthesis as depicted in Method D Step 1: To methyl 4-{2-[2-(2-aminoethyl)-1-benzhydryl-5-chloro-1H-indol-3-yl]ethoxy}benzoate (0.16M, 1.0 equiv.), Step6, Example 1, and triethylamine (2.3 equiv.) in THF was added 2-chloroethanesulfonyl chloride (1.2 eq) dropwise. After 4 h the mixture was poured into brine and extracted with EtOAc. The combined organic phase was dried over magnesium sulfate and purified by column chromatography to afford 75% of the vinyl sulfonamide.

Step2: To the product from step 1 in 1-propanol was added morpholine. After 5 h the reaction mixture was evaporated to dryness before redissolving in EtOAc. The organic phase was washed with brine, dried over magnesium sulfate, and purified by column chromatography to give the desired methyl ester in 89% yield.

Step 3: The ester intermediate was hydrolyzed according to Step 8 Example 1 to afford the title acid in 89% yield. m/z (M-1) 702.17. HRMS calc for [$C_{38}H_{40}ClN_3O_6S$—H] 700.2535 found 700.22500.

EXAMPLE 88

4-(2-{1-Benzhydryl-5-chloro-2-[2(2-pyrazol-1-yl-ethane sulfonylamino)-ethyl]-1H-indol-3-yl}-ethoxy)-benzoic acid Step 1: The compound was prepared from the intermediate from Example 87 step 1 and 1H-pyrazole according to the procedure in Example 87 step 2 except that it was heated at 80° C. for 18 h, in 90% yield.

Step2: The ester intermediate was hydrolyzed according to Step 8 Example 1 to afford the title acid in 61% yield. m/z (M-1) 681.24. HRMS calc for [$C_{37}H_{35}ClN_4O_5S$—H] 681.19439 found 681.19407.

What is claimed is:

1. A method comprising reacting a dihalomethyl compound with a sulfoxide in the absence of an effective amount of an activating reagent to form the corresponding aldehyde, according to the reaction:

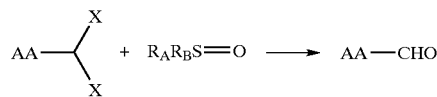

wherein
AA represents an aryl group, or an alkenyl or alkynyl group;
X represents F, Cl, Br, or I; and
$R_A$ and $R_B$ are each an alkyl or aryl group independently selected from the group consisting of $C_1$–$C_6$ alkyl optionally substituted by a $C_4$–$C_8$ cycloalkyl or phenyl group, $C_4$–$C_8$ cycloalkyl optionally substituted by up to two $C_1$–$C_3$ alkyl groups, and phenyl optionally substituted by up to five $C_1$–$C_3$ alkyl groups.

2. A method according to claim 1 wherein AA is selected from the group consisting of phenyl, naphthyl, indolyl, biphenyl, pyridinyl, pyrrolyl, quinolinyl, isoquinolinyl, pyrimidinyl, furyl, oxazolyl, thioazolyl, and isoxazolyl, and straight, branched, cyclic and bicyclic alkenyl and alkynyl groups having from 2 to 12 carbon atoms, each of which may be substituted or unsubstituted.

3. A method according to claim 2 wherein $R_A$ and $R_B$ are each independently selected from the group consisting of phenyl, methyl, ethyl and tetramethylene.

4. A method according to claim 2 wherein AA is selected from the group consisting of phenyl, biphenyl and indolyl, each of which may be substituted or unsubstituted.

5. A method according to claim 1 wherein AA is phenyl or biphenyl optionally substituted by one to three substituents independently selected from the group consisting of halogen, cyano, nitro, hydroxy, $R_C$ alkyl, —C(O)O$R_C$ alkyl, —N$R_CR_D$, —C(O)N$R_CR_D$ amide, S(O)$_2R_CR_D$, N$R_1$C(O)N$R_CR_D$, or —OC(O)N$R_CR_D$ group, where $R_C$ and $R_D$ are each $C_1$–$C_4$ alkyl.

6. A method according to claim 5 wherein AA is phenyl optionally substituted by one substituent selected from the group consisting of halogen, cyano, nitro, hydroxy, $R_C$ alkyl, —C(O)O$R_C$ alkyl, —N$R_CR_D$, —C(O)N$R_CR_D$ amide, S(O)$_2R_CR_D$, N$R_1$C(O)N$R_CR_D$, or —OC(O)N$R_CR_D$ group, where $R_C$ and $R_D$ are each $C_1$–$C_4$ alkyl.

7. A method according to claim 6 wherein said reaction occurs at a temperature in the approximate range of 20–120° C.

8. A method according to claim 1 wherein AA is an optionally substituted 2-indolyl group.

9. A method according to claim 8 wherein AA is

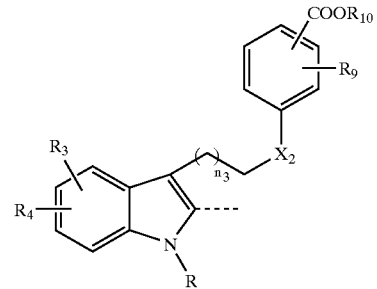

wherein:
R is selected from the formulae —(CH$_2$)$_n$-A, —(CH$_2$)$_n$—S-A, or —(CH$_2$)$_n$—O-A, wherein A is selected from the moieties:

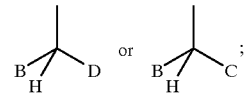

wherein
D is $C_1$–$C_6$ lower alkyl, $C_1$–$C_6$ lower alkoxy, $C_3$–$C_6$ cycloaklyl —CF$_3$ or —(CH$_2$)$_{1-3}$—CF$_3$;
B and C are independently selected from phenyl, pyridinyl, pyrimidinyl, furanyl, thiophenyl or pyrrolyl groups, each optionally substituted by from 1 to 3, preferably 1 to 2, substituents selected independently from H, halogen, —CN, —CHO, —CF$_3$, —OCF$_3$, —OH, $C_1$–$C_6$ alkyl, $C_1$–$C_6$ alkoxy, —NH$_2$, —N(C$_1$–C$_6$)$_2$, —NH(C$_1$–C$_6$), —N—C(O)—(C$_1$–C$_6$), —NO$_2$, and a 5- or 6-membered heterocyclic or heteroaromatic ring containing 1 or 2 heteroatoms selected from O, N or S;

n is an integer from 0 to 3;

$n_3$ is an integer from 0 to 3;

$X_2$ is selected from the group consisting of —O—, —CH$_2$—, —S—, —SO—, —SO$_2$—, —NH—, —C(O)—,

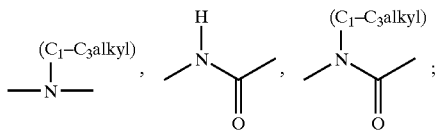

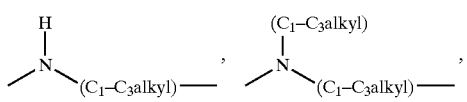

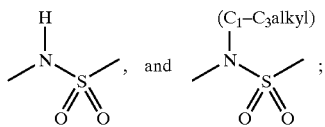

$R_3$ is selected from the group consisting of H, halogen, —CN, —CHO, —CF$_3$, —OCF$_3$, —OH, —C$_1$-C$_6$ alkyl, C$_1$-C$_6$ alkoxy, C$_1$-C$_6$ thioalkyl, —NH$_2$, —N(C$_1$-C$_6$)$_2$, —NH(C$_1$-C$_6$), —N—C(O)—(C$_1$-C$_6$), and —NO$_2$;

$R_4$ is selected from H, halogen, —CN, —CHO, —CF$_3$, —OCF$_3$, —OH, —C$_1$-C$_6$ alkyl, C$_1$-C$_6$ alkoxy, C$_1$-C$_6$ thioalkyl, —NH$_2$, —N(C$_1$-C$_6$)$_2$, —NH(C$_1$-C$_6$), —N—C(O)—(C$_1$-C$_6$), —NO$_2$, —N—C(O)—N(C$_1$-C$_3$ alkyl)$_2$, —N—C(O)—NH(C$_1$-C$_3$ alkyl), —N—C(O)—O—(C$_1$-C$_3$ alkyl), —SO$_2$-C$_1$-C$_6$ alkyl, —S—C$_3$-C$_6$ cycloalkyl, —S—CH$_2$-C$_3$-C$_6$ cycloalkyl, —SO$_2$—C$_3$-C$_6$ cycloalkyl, —SO$_2$—CH$_2$—C$_3$-C$_6$ cycloalkyl, C$_3$-C$_6$ cycloalkyl, —CH$_2$—C$_3$-C$_6$ cycloalkyl, —O—C$_3$-C$_6$ cycloalkyl, —O—CH$_2$—C$_3$-C$_6$ cycloalkyl, phenyl, benzyl, benzyloxy, morpholino or other heterocycles such as pyrrolidino, piperidine, piperizine furan, thiophene, imidazole, tetrazole, pyrazine, pyrazolone, pyrazole, imidazole, oxazole and isoxazole, the rings of each of these $R_4$ groups each being optionally substituted by from 1 to 3 substituents selected from the group of H, halogen, —CN, —CHO, —CF$_3$, —OH, —C$_1$-C$_6$ alkyl, C$_1$-C$_6$ alkoxy, —NH$_2$, —N(C$_1$-C$_6$)$_2$, —NH(C$_1$-C$_6$), —N—C(O)—(C$_1$-C$_6$), —NO$_2$, —SO$_2$(C$_1$-C$_3$ alkyl), —SO$_2$NH(C$_1$-C$_3$ alkyl), —SO$_2$N(C$_1$-C$_3$ alkyl)$_2$, and OCF$_3$;

$R_9$ is selected from the group consisting of H, halogen, —CN, —CHO, —CF$_3$, —OH, —C$_1$-C$_6$ alkyl, C$_1$-C$_6$ alkoxy, —NH$_2$, —N(C$_1$-C$_6$)$_2$, —NH(C$_1$-C$_6$), —N—C(O)—(C$_1$-C$_6$), and —NO$_2$; and, $R_{10}$ is a C$_1$-C$_6$ alkyl group.

10. A method according to claim 9 wherein $R_A$ and $R_B$ are each independently selected from the group consisting of phenyl, methyl, ethyl and tetramethylene.

11. A method according to claim 10 wherein $R_A$ and $R_B$ are each methyl.

12. A method according to claim 11 wherein said reaction occurs at a temperature in the approximate range of 15–35° C.

13. A method according to claim 11 further comprising:

a) reacting said aldehyde with nitromethane and a catalytic amount of ammonium acetate, followed by reduction with a Zn(Hg) amalgam to convert the —CHO group to an ethylamine group;

b) reacting the ethylamine compound with ClSO$_2$(CH$_2$)$_{n2}$ X$_1$R$_1$, wherein $R_1$ is a moiety selected from C$_1$-C$_6$ alkyl, C$_1$-C$_6$ fluorinated alkyl, C$_3$-C$_6$ cycloalkyl, tetrahydropyranyl, camphoryl, adamantyl, CN, —N(C$_1$-C$_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7,dimethyl-bicyclo[ 2.2.1]heptan-2-one, Benzo[1,2,5]oxadiazole, 2-Oxa-5-aza-bicyclo[ 2.2.1]heptane, Piperazin-2-one or pyrrolyl groups, each optionally substituted by from 1 to 3, preferably 1 to 2, substituents independently selected from H, halogen, —CN, —CHO, —CF$_3$, OCF$_3$, —OH, —C$_1$-C$_6$ alkyl, C$_1$-C$_6$ alkoxy, —NH$_2$, —N(C$_1$-C$_6$)$_2$, —NH (C$_1$-C$_6$), —N—C(O)—(C$_1$-C$_6$), —NO$_2$, —SO$_2$ (C$_1$-C$_3$ alkyl), —SO$_2$NH$_2$, —SO$_2$NH(C$_1$-C$_3$ alkyl), —SO$_2$N(C$_1$-C$_3$ alkyl)$_2$, —COOH, —CH$_2$—COOH, —CH$_2$—N(C$_1$-C$_6$ alkyl), —CH$_2$—N(C$_1$-C$_6$ alkyl)$_2$, —CH$_2$—NH$_2$, pyridine, 2-Methyl-thiazole, morpholino, 1-Chloro-2-methyl-propyl, —C$_1$-C$_{1-6}$ thioalkyl, phenyl (further optionally substituted with halogens), benzyloxy, (C$_1$-C$_3$ alkyl)C(O)CH$_3$, (C$_1$-C$_3$ alkyl)OCH$_3$, C(O)NH$_2$, and

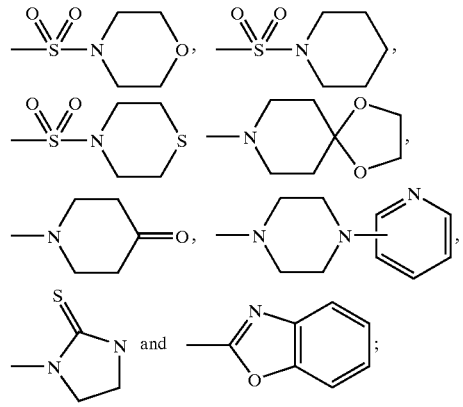

$X_1$ is selected from a chemical bond, —S—, —O—, —S(O)—, —S(O)$_2$—, —NH—, —NHC(O)—, —C=C—,

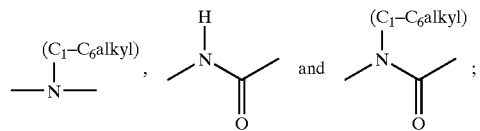

and, $n_2$ is an integer from 0 to 4, to form a final compound of formula
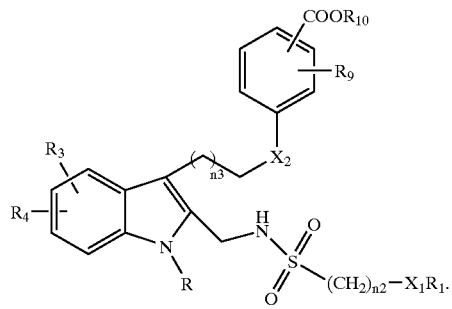
14. The method of claim 13 further comprising hydrolyzing the ester group of the final compound to form a compound of the formula
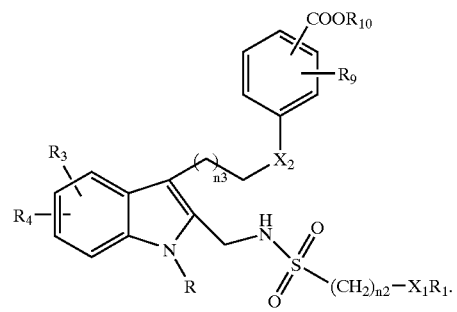
* * * * *